United States Patent
Liu

(10) Patent No.: US 11,332,747 B2
(45) Date of Patent: May 17, 2022

(54) BISPECIFIC APTAMER FOR TREATING CANCER

(71) Applicant: Augusta University Research Institute, Inc., Augusta, GA (US)

(72) Inventor: Hongyan Liu, Martinez, GA (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 936 days.

(21) Appl. No.: 15/899,473

(22) Filed: Feb. 20, 2018

(65) Prior Publication Data

US 2020/0157542 A1    May 21, 2020

Related U.S. Application Data

(60) Provisional application No. 62/462,993, filed on Feb. 24, 2017.

(51) Int. Cl.
| | | |
|---|---|---|
| *C12N 15/115* | (2010.01) | |
| *A61K 48/00* | (2006.01) | |
| *A61P 35/00* | (2006.01) | |

(52) U.S. Cl.
CPC ............ *C12N 15/115* (2013.01); *A61P 35/00* (2018.01); *A61K 48/00* (2013.01)

(58) Field of Classification Search
None
See application file for complete search history.

(56) References Cited

U.S. PATENT DOCUMENTS

| | | | | |
|---|---|---|---|---|
| 2010/0273160 | A1* | 10/2010 | Donahoe ................ | A61K 45/06 435/6.18 |
| 2011/0165123 | A1* | 7/2011 | Hartmann ................ | A61P 31/04 424/85.6 |
| 2018/0037892 | A1* | 2/2018 | Shigdar ............... | A61K 31/7088 |

FOREIGN PATENT DOCUMENTS

WO    WO-2016127216 A1 * 8/2016 ........... C12N 15/115

OTHER PUBLICATIONS

Dalerba et al. PNAS 104, 10158-101634 (Year: 2007).*
Zheng et al. (Theranostics 2017 (Mar. 23, 2017), vol. 7, pp. 1373-1388) (Year: 2017).*
Ababneh, Nidaa et al., "in Vitro Selection of Modified RNA Aptamers Against CD44 Cancer Stem Cell Marker", Nucleic Acid Ther, 23:401-407 (2013).
Alshaer, Walhan et al., "Functionalizing Liposomes with Anti-CD44 Aptamer for Selective Targeting of Cancer Cells", Bioconjug Chem, 26:1307-1313 (2015).
Baeuerle, P.A., et al., "EpCAM (CD326) Finding its Role in Cancer", Br J Cancer, 96:417-423 (2007).
Balzar, M., et al., "The Biology of the 17-1A Antigen (Ep-CAM)", J Mol Med (Berl), 77:699-712 (1999).
Barnd, Donna L., et al., "Specific, Major Histocompatibility Complex-Unrestricted Recognition of Tumor-Associated Mucins by Human Cytotoxic T Cells", Proc Nat Acad Sci USA, 86:7159 (1989).
Bast, Robert C., et al., "A Radioimmunoassay Using a Monoclonal Antibody to Monitor the Course of Epithelial Ovarian Cancer", N Eng J Med, 309:883 (1983).
Berezhnoy, Alexey et al., "Aptamer-Targeted Inhibition of mTOR in T Cells Enhances Antitumor Immunity", J Clin Invest, 124:188-197 (2014).
Bock, Louis C., et al., "Selection of Single-Stranded DNA Molecules that Bind and Inhibit Human Thrombin", Nature, 355:564-566 (1992).
Bowtell, David D., et al., "Rethinking Ovarian Cancer II: Reducing Mortality from High-Grade Serous Ovarian Cancer", Nat Rev Cancer, 15:668-679 (2015).
Burges, Alexander et al., "Effective Relief of Malignant Ascites in Patients with Advanced Ovarian Cancer by a Trifunctional Anti-EpCAM x Anti-CD3 Antibody: A Phase I/II Study", Clin Cancer Res, 13:3899-3905 (2007).
Dassie, Justin P., et al., "Systemic Administration of Optimized Aptamer-siRNA Chimeras Promotes Regression of PSMA-Expressing Tumors", Nat Biotechnol, 27.839-849 (2009).
Dassie, Justin P., et al., "Current Progress on Aptamer-Targeted Oligonucleotide Therapeutics", Ther Deliv, 4:1527-1546 (2013).
Ellington, Andrew D., et el., "In Vitro Selection of RNA Molecules that Bind Specific Ligands", Nature, 345:818-822 (1990).
Gardner, M.J., et al., "Human Ovarian Tumour Cells Can Bind Hyaluronic Acid via Membrane CD44: A Possible Step in Peritoneal Metastasis", Clin Exp Metastasis, 14:325-334 (1996).
Gebauer, Gerhard et al., "Tumor Marker Concentrations in Normal and Malignant Tissues of Colorectal Cancer Patients and their Prognostic Relevance", Anticancer Res, 17(4B):2939 (1997).
Hirokawa, Shinichiro et al., "Neuroblastoma in an Adult with a High Serum Level of Carbohydrate Antigen, CA125: Report of a Case", Surg Today, 28:349 (1998).
Huang, Yuanyu et al., "Systemic Administration of siRNA via cRGD-Containing Peptide", Sci Rep, 5:12458 (2015).
Imrich, Sannia et al., "EpCAM and its Potential Role in Tumor-Initiating Cells", Cell Adh Migr, 6:30-38 (2012).
Jayson, Gordon C., et al., "Ovarian Cancer", Lancet, 384:1376-1388 (2014).
Keefe, Anthony D., et al., "Aptamers as Therapeutics", Nat Rev Drug Discov, 9:537-550 (2010).
Kim, Ayako et el., "Therapeutic Strategies in Epithelial Ovarian Cancer", J Exp Clin Cancer Res, 31:14 (2012).
Kontermann, Roland E., "Dual Targeting Strategies with Bispecific Antibodies", mAbs, 4:182-197 (2012).
Kudoh, Kazuya et al., "Preoperative Determination of Several Serum Tumor Markers in Patients with Primary Epithelial Ovarian Carcinoma", Gynecol Obstet Invest, 47:52 (1999).

(Continued)

*Primary Examiner* — Brian Whiteman
(74) *Attorney, Agent, or Firm* — Smith, Gambrell & Russell; Judy Jarecki-Black

(57) ABSTRACT

Bispecific aptamers having a first end that specifically binds to a first tumor specific marker, tumor antigen, or viral protein and a second end that specifically binds to a second tumor specific marker, tumor antigen, or viral protein are provide. The bispecific aptamers can be used to treat cancer or virally infected cells. Generally, the bispecific aptamers bind to two surface proteins, preferably different proteins, on the same cell. In a preferred embodiment the bispecific aptamers bind to two different tumor markers, tumor antigens, tumor specific proteins and combinations thereof.

8 Claims, 25 Drawing Sheets

Specification includes a Sequence Listing.

(56) References Cited

OTHER PUBLICATIONS

Lindhofer, H., et al., "Preferential Species-Restricted Heavy/Light Chain Pairing in Rat/Mouse Qusdromas. Implications for a Single-Step Purification of Bispecific Antibodies.", J Immunol, 156:219-225 (1995).

Liu, Hong Yan et al., "Co-Targeting EGFR and Survivin with a Bivalent Aptamer-Dual siRNA Chimera Effectively Suppresses Prostate Cancer", Sci Rep, 6:30346 (2016).

Liu, Li et al., "Self-Assembled Nanoparticles Based on the c(KGDfk) Peptide for the Delivery of siRNA Targeting the VEGFR2 Gene for Tumor Therapy", Int J Nanomedicine, 9:3509-3526 (2014).

Lloyd, Kenneth O., et al., "Isolation and Characterization of Ovarian Cancer Antigen CA125 Using a New Monoclonal Antibody (VK-8): Identification as a Mucin-Type Molecule", Int J Canc, 71:842 (1997).

Mack, Matthias et al., "A Small Bispecific Antibocy Construct Expressed as a Functional Single-Chain Molecule with High Tumor Cell Cytotoxicity", Proc Natl Acad Sci USA, 92:7021-7025 (1995).

Meier, Warner et al., "Prognostic Significance of CA125 in Patients with Ovarian Cancer and Secondary Debulking Surgery", Anticancer Res, 17(4B):2945 (1997).

Nunna, Suneetha et al., "Targeted Methylation of the Epithelial Cell Adhesion Molecule (EpCAM) Promoter to Silence its Expression in Ovarian Cancer Cells", PLOS One, 9:87703 (2014).

Orian-Rousseau, Véronique, "CD44 Acts as a Signaling Platform Controlling Tumor Progression and Metastasis", Frontiers in Immunology, 6:154 (2015).

Reichert, Janice M., et al., "Development Trends for Monoclonal Antibody Cancer Therapeutics", Nat Rev Drug Discov, 6:349-356 (2007).

Sacks, Joelle D., et al., "Expression and Function of CD44 in Epithelial Ovarian Carcinoma", Biomolecules, 5.3051-3066 (2015).

Sarandakou, Angeliki et al., "Vaginal Fluid and Serum CEA, CA125 and SCC in Normal Conditions and in Benign and Malignant Diseases of the Genital Tract". Acta Oncol, 36:755 (1997).

Sarandakou, A., et al., "Tumour-Associated Antigens CEA, CA125, SCC and TPS in Gynaecological Cancer", Eur J Gynaecol Oncol, 19:73 (1998).

Shigdar, Sarah et al., "RNA Aptamer Against a Cancer Stem Cell Marker Epithelial Cell Adhesion Molecule", Cancer Sci, 102:991-998 (2011).

Strobel, Thomas et al., "In Vivo Inhibition of CD44 Limits Intra-Abdominal Spread of a Human Ovarian Cancer Xenograft in Nude Mice: A Novel Role for CD44 in the Process of Peritoneal Implantation", Cancer Res, 57:1228-1232 (1997).

Sun, Hongguang et al., "Oligonucleotide Aptamers: New Tools for Targeted Cancer Therapy", Mol Ther Nucleic Acids, 3:e182 (2014).

Tsikouras, Panagiotis et al., "The Contribution of Calumaxomab in the Treatment of Malignant Ascites in Patients with Ovarian Cancer: A Review of the Literature", Arch Gynecol Obstet, 288:581-585 (2013).

Van Der Veeken, J., et al., "Crosstalk Between Epidermal Growth Factor Receptor- and Insulin-Like Growth Factor-1 Receptor Signaling: Implications for Cancer Therapy", Current Cancer Drug Targets, 9:748-760 (2009).

Wang, Huimin et al., "Expression and Significance of GD44, CD47 and c-met in Ovarian Clear Cell Carcinoma", Int J Mol Sci, 16:3391-3404 (2015).

Wang, Tao et al., "EpCAM Aptamer-Mediated Survivin Silencing Sensitized Cancer Stem Cells to Doxorubicin in a Breast Cancer Model", Theranostics, 5:1456-1472 (2015).

Wong, Tien Y., et al., "Clinical Update: New Treatments for Age-Related Macular Degeneration". Lancet, 370:204-206 (2007).

Wu, Chengbin et al., "Simultaneous Targeting of Multiple Disease Mediators by a Dual-Variable-Domain Immunoglobulin", Nat Biolechnol, 25.1290-1297 (2007).

Xiang, Wei et al., "Cytotoxic Activity of Novel Human Monoclonal Antibody MT201 Against Primary Ovarian Tumor Cells", J Cancer Res Clin Oncol, 129:341-348 (2003).

Zhang, MD, PhD., Jing et al., "CD44 Standard Form Expression is Correlated with High-Grade and Advanced-Stage Ovarian Carcinoma but not Prognosis", Human Pathology, 44:1882-1889 (2013).

Zhou, Jiehua et al., "Current Progress of RNA Aptamer-Based Therapeutics", Front Genet, 3:234 (2012).

Zou, I., et al., "Efficient Inhibition of Intraperitoneal Human Ovarian Cancer Growth by Short Hairpin RNA Targeting CD44", Neoplasma. 61:274-282 (2014).

* cited by examiner

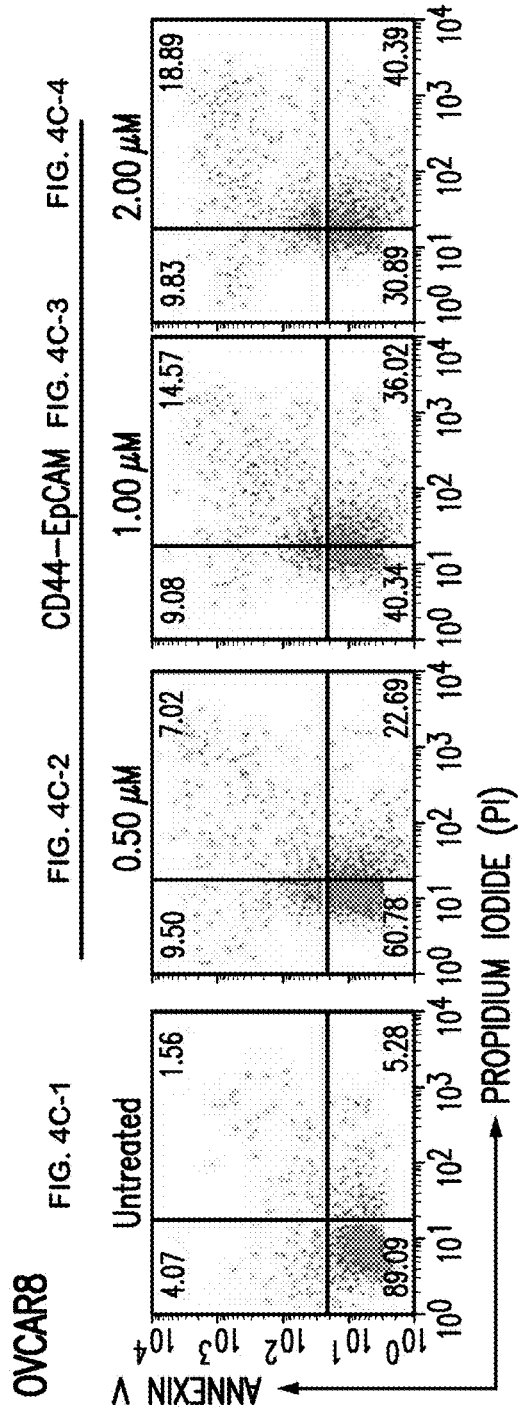
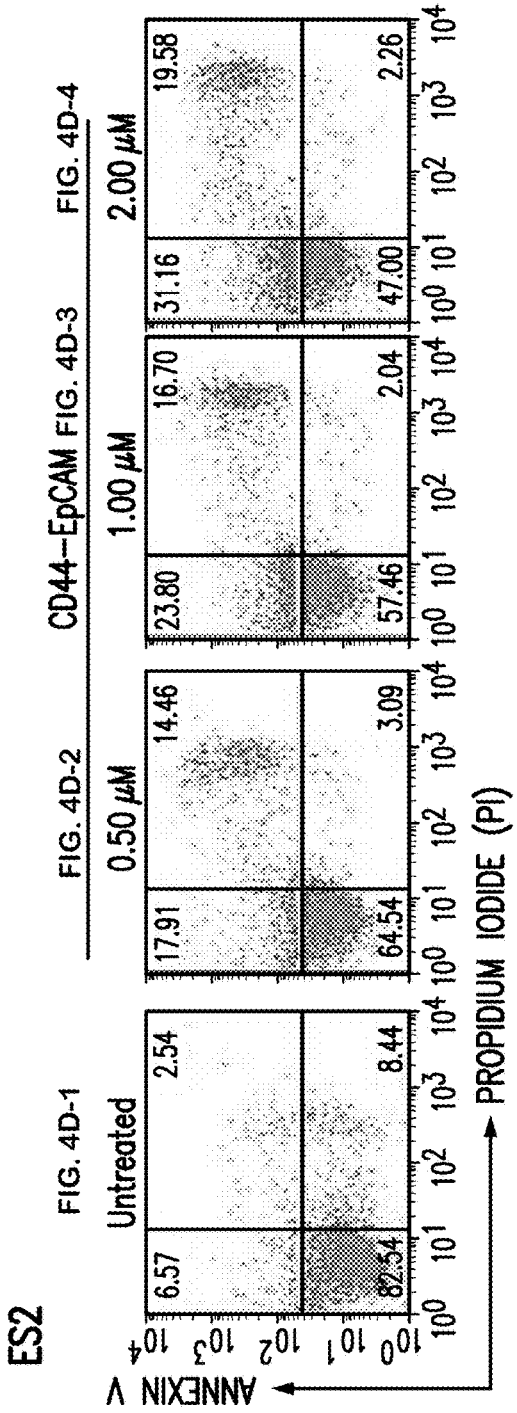
FIG. 4C
FIG. 4D

1. Heart  2. Lung  3. Liver  4. Spleen  5. Muscle  6. Kidney  7. Brain  8. Stomach and intestine 1. Heart  2. Lung  3. Liver  4. Spleen  5. Muscle  6. Kidney  7. Brain  8. Stomach and intestine

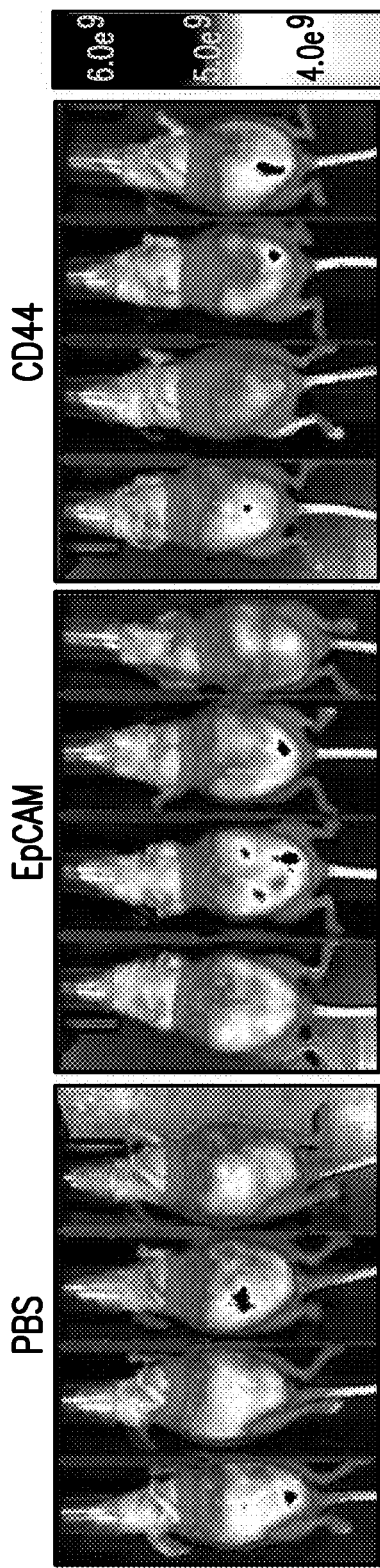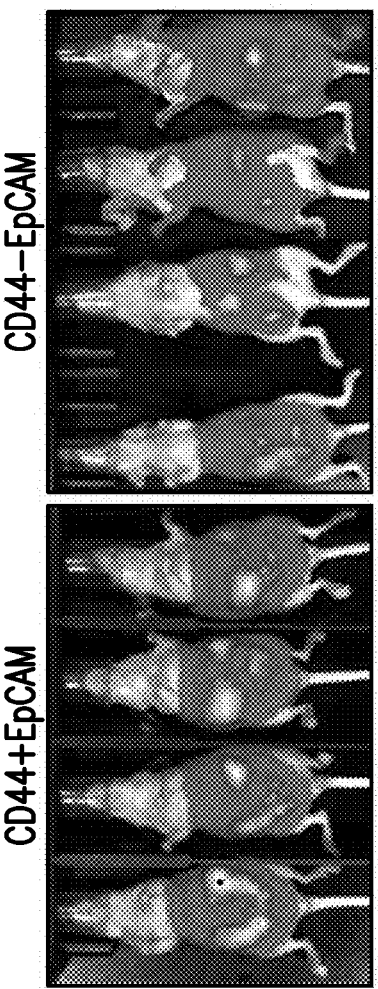
FIG. 6A  FIG. 6B  FIG. 6C  FIG. 6D  FIG. 6E

SEQUENCE LISTING

```
<160> NUMBER OF SEQ ID NOS: 17

<210> SEQ ID NO 1
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gggatggatc caagcttact ggcatctgga tttgcgcgtg ccagaataaa gagtataacg    60
tgtgaatggg aagcttcgat aggaattcgg                                    90

<210> SEQ ID NO 2
<211> LENGTH: 37
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 2
taatacgact cactataggg atggatccaa gcttact                              37

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aatttcatct cctgaacaag cttttccgaa t                                   31

<210> SEQ ID NO 4
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
taatacgact cactatgcga ctggttaccc ggtcgtaaaa tttcatctcc tgaacaagct     60
t                                                                    61

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taatacgact cactatagcg actggtta                                       28

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagcttgttc aggagatgaa attttacga                                      29

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
taatacgact cactatgcga ctggttaccc ggtcgtaaaa tttcatctcc tgaacaagct     60
ttt                                                                  63
```

```
<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (36)..(38)
<223> OTHER INFORMATION: This region may or may not be present

<400> SEQUENCE: 8
taatacgact cactatgcga ctggttaccc ggtcgtaaaa tttcatctcc tgaacaagct    60
ttt                                                                 63

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
taatacgact cactatagcg actggtta                                      28

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaagcttgt tcaggagatg aaatt                                         25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aatttcatct cctgaacaag ctt                                           23

<210> SEQ ID NO 12
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggaucccgac uggcgagagc cagguaacga auggaucc                           38

<210> SEQ ID NO 13
<211> LENGTH: 115
<212> TYPE: RNA
<213> ORGANISM: Artificial Sequence
<220> FEATURE:
<223> OTHER INFORMATION: Description of Artificial Sequence: Synthetic
      polynucleotide
```

```
<400> SEQUENCE: 13
gggauggauc caagcuuacu ggcaucugga uuugcgcgug ccagaauaaa gaguauaacg      60
ugugaauggg aagcuucgau aggaauucgg aaaagcuugu ucaggagaug aaauu         115

<210> SEQ ID NO 14
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gcgacugguu acccggucgu aaaauuucau cuccugaaca agcuu                     45

<210> SEQ ID NO 15
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gcgacugguu acccggucgu aaaauuucau cuccugaaca agcuuuu                   47

<210> SEQ ID NO 16
<211> LENGTH: 113
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 16
gggauggauc caagcuuacu ggcaucugga uuugcgcgug ccagaauaaa gaguauaacg      60
ugugaauggg aagcuucgau aggaauucgg aagcuuguuc aggagaugaa auu           113

<210> SEQ ID NO 17
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gcgacugguu acccggucga auuucaucuc cugaacaagc uu                        42
```

BISPECIFIC APTAMER FOR TREATING CANCER

STATEMENT REGARDING FEDERALLY SPONSORED RESEARCH

This invention was made with government support under W81XWH-15-1-0333 awarded by the Department of Defense. The government has certain rights in the invention.

TECHNICAL FIELD OF THE INVENTION

The invention is generally directed to nucleic acids for the treatment of cancer, namely bispecific aptamers for the treatment of cancer.

SEQUENCE LISTING

The instant application contains a Sequence Listing which has been submitted electronically in ASCII format and is hereby incorporated by reference in its entirety. Said ASCII copy, created on May 19, 2021, is named 064466_066_SL.txt and is 4.66 kilobytes in size.

BACKGROUND OF THE INVENTION

Ovarian cancer (OC) is the most deadly cancer among all gynecologic malignancies. OC is often detected at an advanced stage with wide peritoneal metastasis. The 5-year survival rate of advanced OC is around 20-30% (Bowtell, et al., *Nat Rev Cancer*, 15:668-679 (2015)). The combination of debulking and platinum-based chemotherapy is the standard treatment for advanced OC. Although patients initially respond favorably, most of them will develop chemoresistance and eventually die with peritoneal metastasis (Jayson et al., *Lancet*, 384:1376-1388 (2014); Kim et al., *J Exp Clin Cancer Res*, 31:14 (2012)). Therefore, there is an urgent need to develop effective therapeutics to overcome chemoresistance and to inhibit peritoneal metastasis.

Combination therapy by simultaneously blocking two or more signaling pathways (Wu et al., *Nat Biotechnol*, 25:1290-1297 (2007)) has demonstrated promise in suppressing tumor progression and metastasis due to the capacity to overcome the functional redundancy or synergistic action of targeted molecules (van der Veeken, et al., *Current Cancer Drug Targets*, 9:748-760 (2009)). Bispecific antibodies that can simultaneously target two different molecules have outshined conventional monoclonal antibody by exhibiting better therapeutic efficacy and inciting less drug resistance (Kontermann, *Mabs*, 4:182-197 (2012)). The two-in-one format of bispecific molecules offers less complicated drug administration and has received more favorable regulatory approval than the proposed use of two single molecules in combination. However, antibody-based bispecific molecules exhibit high immunogenicity and are difficult to produce due to complicated technologies such as hybrid-hybridoma (Lindhofer, et al., *J. Immunol*, 155:219-225 (1995)) and genetic engineering (Mack, et al., *Proc Natl Acad Sci USA*, 92:7021-7025 (1995)).

Aptamers are ssDNA or ssRNA that can bind a target with high affinity and specificity (Sun, et al., *Mol Ther Nucleic Acids*, 3:e182 (2014)). Potent aptamers can be generated through in vitro enrichment process (Ellington, et al., *Nature*, 346:818-822 (1990); Bock, et al., *Nature*, 355:564-566 (1992)) and are usually produced with little batch-to-batch variation (Dassie, et al., *Ther Deliv*, 4:1527-1546 (2013); Zhou, et al., *Front Genet*, 3:234 (2012)). The nature of an aptamer as a small oligonucleotide implicates that it offers many advantages over the antibody such as cell-free chemical synthesis, non-immunogenicity, high tissue penetration, thermostability and low cost (Dassie, et al., *Ther Deliv*, 4:1527-1546 (2013); Dassie, et al., *Nat Biotechnol*, 27:839-849 (2009); Berezhnoy, et al., *J Clin Invest*, 124: 188-197 (2014); Keefe, et al., *Nat Rev Drug Discov*, 9:537-550 (2010); Liu, et al., *Sci Rep*, 6:30346 (2016)). Pegaptanib, a vascular endothelial growth factor-targeted aptamer, is approved for treating age-related macular degeneration (Wong, et al., *Lancet*, 370:204-206 (2007)). A single EpCAM aptamer consisting of 19-nt RNA possesses similar binding affinity as antibodies and is efficiently internalized through receptor-mediated endocytosis (Shigdar, et al., *Cancer Sci*, 102:991-998 (2011); Wang, et al., *Theranostics*, 5:1456-1472 (2015)). A single CD44 aptamer with 90-nt has also been produced and can effectively target cells with high CD44 expression (Ababneh, et al., *Nucleic Acid Ther*, 23:401-407 (2013)). Importantly, single CD44 aptamer has shown capacity for drug delivery (Alshaer, et al., *Bioconjug Chem*, 26:1307-1313 (2016)). However, the therapeutic effect of these two aptamers against tumorigenesis has not been reported.

SUMMARY OF THE INVENTION

Bispecific aptamers having a first end that specifically binds to a first tumor specific marker, tumor antigen, or viral protein and a second end that specifically binds to a second tumor specific marker, tumor antigen, or viral protein are provide. The bispecific aptamers can be used to treat cancer or virally infected cells. Generally, the bispecific aptamers bind to two surface proteins, preferably different proteins, on the same cell. In a preferred embodiment the bispecific aptamers bind to two different tumor markers, tumor antigens, tumor specific proteins, and combinations thereof.

One embodiment provides an RNA-based bispecific molecule formed by fusing single CD44 and EpCAM aptamers into one unit. This fused aptamer displayed significantly improved circulation half-life and reduced renal filtration compared to the single aptamers. The bispecific CD44-EpCAM aptamer inhibited ovarian cancer cell growth and suppressed intraperitoneal tumor progression much more efficiently than single CD44 and EpCAM aptamers used either alone or in combination.

BRIEF DESCRIPTION OF THE DRAWINGS

(FIG. 1A) Schematic illustration of the structure of CD44-EpCAM aptamer. EpCAM aptamer (SEQ ID NO:14) was conjugated with CD44 aptamer (SEQ ID NO:13) through 23 bp adaptor and 2-3 unpaired base linkers. (FIG. 1B) Schematic of ELISA for evaluation of dual specificity of CD44-EpCAM aptamer. (FIG. 1C) A line graph representing concentration of CD44 protein (nM) in CD44-EpCAM and CD44+EpCAM samples. The X-axis represent concentration (nM) and the Y-axis represents absorbance (OD450). (FIG. 1D) A line graph representing concentration of human serum albumin (nM) in CD44-EpCAM samples. The X-axis represents concentration (nM) and the Y-axis represents absorbance (OD450).

(FIG. 2A) Western blot analysis of protein expression of CD44 and EpCAM in ovarian cancer cell lines (OVCAR8, SKOV3, OCC, and ES2) and normal HEK293T cells. (FIGS. 2B-2F) Line graphs representing cell viability of ovarian cancer cell lines including (Figure. 2B) OVCAR8, (FIG. 2C) SKOV3, (FIG. 2D) OCC1, (FIG. 2E) ES2 and (FIG. 2F) normal HEK293T cells treated with varying concentrations (μM) of MG (▲), CD44 (x), EpCAM (♦), CD44+EpCAM (●), or CD44-EpCAM (■). The X-axis represents concentration (μM) and the Y-axis represents cell viability (%).

(FIG. 3A) Agarose gel electrophoresis image showing expression levels of unmodified and 2'-fluoro-modified CD44-EpCAM in 50% human serum incubated for 2 h, 6 h, or 24 h. (FIG. 3B) Bar graph showing quantification of 2'-fluoro-modified CD44-EpCAM in human serum and non-serum samples. (FIGS. 3C-3G) Histograms showing binding pattern of (FIG. 3C) OVCAR8, (FIG. 3D) SKOV3, (FIG. 3E) ES2, (FIG. 3F) OCC1, or (FIG. 3G) HEK293T cells with CD44-EpCAM by flow cytometry. Unstained cells (▨), MG stained cells(___), and CD44-EpCAM stained cells (——). (FIG. 3H) Western blot analysis of CD44 and/or EpCAM gene knockdown. (FIG. 3I) Histogram showing cell binding of OVCAR cells with CD44-EpCAM. Untreated: (▨); MG-Cy5: (——); normal cells stained with CD44-EpCAM-Cy5: (- - -); CD44 silenced cells stained with CD44-EpCAM-Cy5 (——); EpCAM silenced cells stained with CD44-EpCAM-Cy5: (——); both CD44 and EpCAM silenced cells stained with CD44-EpCAM-Cy5: (- - -).

FIGS. 4A-4F show the evaluation of Apoptosis. (FIG. 4A) Western blot analysis of Caspase-3 expression in OVCAR8 cells after treatment with the varying concentrations of CD44-EpCAM for 48 h or 72 h. (FIG. 4B) Western blot analysis of Caspase-3 expression in ES2 cells after treatment with the varying concentrations of CD44-EpCAM for 72 h. (FIGS. 4C-1-4C-4) Dot plot cytograms showing flow cytometry analysis of apoptosis in OVCAR8 cells after CD44-EpCAM treatment. (FIG. 4C-1) Untreated OVCAR8 cells. (FIGS. 4C-2-4C-4) OVCAR8 cells treated with 0.50 μM, 1.00 μM, and 2.00 μM of CD44-EpCAM respectively. (FIGS. 4D-1-4D-4) Dot plot cytograms showing flow cytometry analysis of apoptosis in ES2 cells after CD44-EpCAM treatment. (FIG. 4D-1) Untreated ES2 cells. (FIGS. 4D-2-4D-4) ES2 cells treated with 0.50 μM, 1.00 μM, and 2.00 μM of CD44-EpCAM respectively. (FIGS. 4E-1-4E-4) Fluorescence micrographs confirming the increase of apoptotic and dead OVCAR8 cells. (FIG. 4E-1) Untreated OVCAR8 cells. (FIGS. 4E-2-4E-4) Increased number of PI and Annexin V+stained dead OVCAR8 cells visualized upon CD44-EpCAM treatment. (FIGS. 4F-1-4F-4) Fluorescence micrographs confirming the increase of apoptotic and dead ES2 cells. (FIG. 4F-1) Untreated ES2 cells (FIGS. 4F-2-4F-4) Increased number of PI and Annexin V+stained dead ES2 cells visualized upon CD44-EpCAM treatment.

(FIGS. 5A-1-5A-3) Cy5 fluorescence whole body scan image of athymic nu/nu female mice intraperitoneally injected with luciferase-expressing OVCAR8 cells. Cy5 fluorescence of whole body was captured at the time points of 0.5 h, 4 h and 8 h after injection with Cy5-CD44-EpCAM aptamer or non-targeting control aptamers. (FIG. 5B) Representative image of bioluminescence captured at 8 h post aptamer injection. (FIG. 5C) Representative image of aptamer localization within ex vivo organs from mice injected with Cy5-CD44-EpCAM aptamer or non-targeting control aptamers. (FIG. 5D) Representative bioluminescence image of aptamer localization within ex vivo organs from mice injected with Cy5-CD44-EpCAM aptamer or non-targeting control aptamers.

FIGS. 6A-6F show that CD44-EpCAM suppresses tumor peritoneal metastasis in xenograft mouse model. (FIGS. 6A-6E) Representative body scan images of athymic nu/nu female mice intraperitoneally injected with luciferase-expressing OVCAR8 cells and treated with (FIG. 6A) PBS, (FIG. 6B) EpCAM, (FIG. 6C) CD44, (FIG. 6D) CD44+ EpCAM, or (FIG. 6E) CD44-EpCAM 5-days post tumor cell implantation. (FIG. 6F) Bar graph showing values of photo flux (photons/sec/m$^2$) in tumor bearing mice treated with PBS, EpCAM, CD44, CD44+EpCAM, or CD44-EpCAM.

(FIG. 7A) Formalin-fixed paraffin-embedded sections of xenograft tumors analyzed with H&E staining, IHC and TUNEL assay. Scale bar 50 μM. IHC staining assays showed that Tumor tissue treated with CD44-EpCAM aptamer increased E-Cadherin and reduced N-Cadherin. (FIGS. 7B-7F) Bar graphs representing the average staining intensity of (FIG. 7B) cleaved caspase 3, (FIG. 7C) Ki67, (FIG. 7D) E-cadherin, (FIG. 7E)N-cadherin, or (FIG. 7F) TUNEL, in tumor tissue from mice treated with PBS, EpCAM, CD44, CD44+EpCAM, or CD44-EpCAM.

(FIG. 8A) Histology examination of CD44-EpCAM's effect on spleen, lung, liver, kidney, heart, intestine and muscle compared with PBS-treated and naïve mouse tissues through H&E staining. (FIG. 8B) Bar graph showing the concentration of IFNα in human peripheral blood mononuclear cells treated with different concentrations of CD44-EpCAM. (FIG. 8C) Bar graph showing the concentration of TNFα (pg/ml) in human peripheral blood mononuclear cells treated with different concentrations of CD44-EpCAM.

(FIGS. 9A-9C) schematic of CD44-Ep-CAM and no linker controls. (FIG. 9A) Linker containing CD44-EpCAM (CD44 aptamer (SEQ ID NO: 13) linked to the EpCAM aptamer (SEQ ID NO:14)); (FIG. 9B) CD44-EpCAM-No linker-1, two "U"s (underlined) were added to the 3-termini of EpCAM aptamer-adaptor (SEQ ID NO:15) to pair with two "A" of the CD44 aptamer (SEQ ID NO:14); (FIG. 9C) CD44-EpCAM-No linker-2, two "U"s were added to 3-termini of EpCAM aptamer-adaptor to pair with two "A", and three single base AAU by which the unpaired base linker between EpCAM aptamer and double stranded adaptor were removed (CD44 aptamer (SEQ ID NO: 16) linked to the EpCAM aptamer (SEQ ID NO:17)). (FIG. 9D) Line graph showing cell viability in OVCAR8 cells treated with varying concentrations of CD44-EpCAM aptamer (■) and no linker control 1 (▲) or no linker control 2 (●) for 72 h.

DETAILED DESCRIPTION OF THE INVENTION

I. Definitions

Figure 1A:
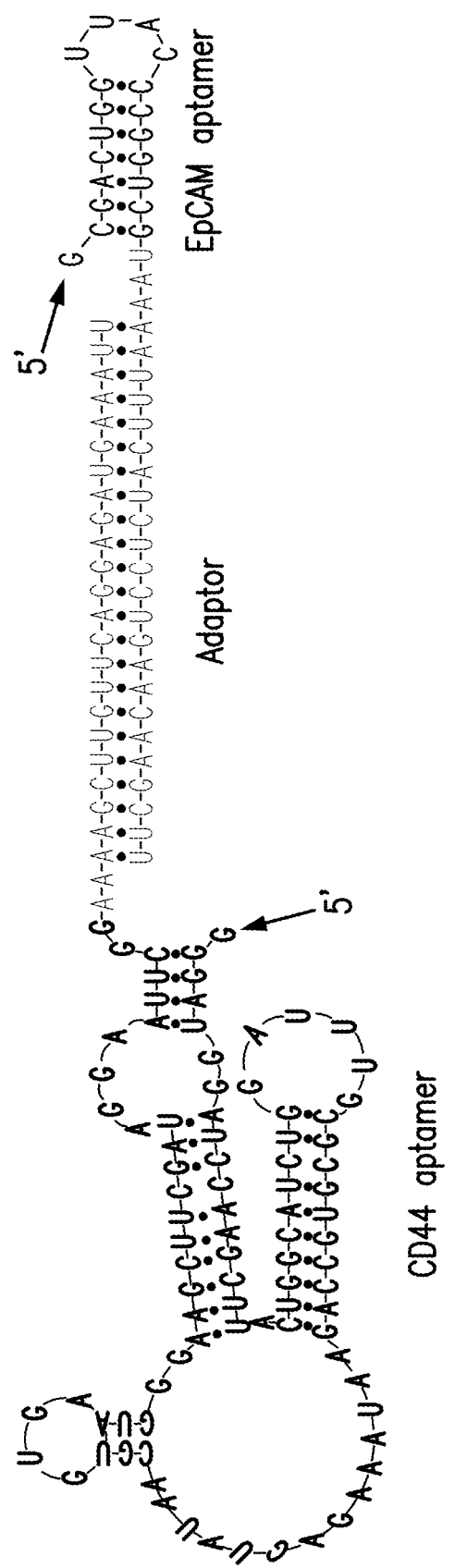
FIGS. 1A-1D show the design and characterization of bispecific CD44-EpCAM aptamer.

The term "tumor marker" or "tumor specific marker" refers to substances that are produced by cancer or by other cells of the body in response to cancer. Most tumor markers are made by normal cells as well as by cancer cells; however, they are produced at much higher levels in cancerous conditions. These substances can be found in the blood, urine, stool, tumor tissue, or other tissues or bodily fluids of some patients with cancer. Most tumor markers are proteins.

A "subject" or "patient" refers to a human, primate, non-human primate, laboratory animal, farm animal, livestock, or a domestic pet.

II. Bispecific Aptamers

Bispecific aptamers are provided that specifically bind to two different tumor markers or tumor antigens or two different proteins that are expressed on the surface of a tumor cell. In certain embodiments, the bispecific aptamers have a detectable label or have a cytotoxic agent conjugated to the bispecific aptamers. In a preferred embodiment, the bispecific marker binds specifically to CD44 and EpCAM.

A. Targeted Cell Surface Proteins

The bispecific aptamers can specifically bind to two different cell surface proteins or peptides expressed on the surface of the cell or secreted into the microenvironment of cell to be treated, for example a cancer cell, tumor cell, or virally infected cell. In some embodiments, the protein or peptide that is specifically recognized by the aptamers of the bispecific aptamers can be cell surface proteins involved in signal transduction, tumor specific antigens, tumor neovasculature antigens, viral proteins or viral peptides displayed in the surface of cells, cytokines, and cytokine receptors. These targeted proteins or peptides may be substances produced by a cell or may be substances which accumulate at a cell microenvironment site, or on cell surfaces.

1. Tumor Specific Antigens

The disclosed aptamers may be specific to or selective for a variety of cell surface or disease-associated antigens. In certain embodiments, such as treating tumors, the aptamers of the disclosed compositions specifically bind one or more tumor-associated antigens. These antigenic markers may be substances produced by a tumor or may be substances which accumulate at a tumor site, or on tumor cell surfaces.

In some embodiments, the targeting domains bind to antigens, ligands or receptors that are specific to tumor cells or tumor-associated neovasculature, or are upregulated in tumor cells or tumor-associated neovasculature compared to normal tissue.

a. Oncogenes

Tumor-associated antigens that are targeted by the disclosed compositions may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.).

Genes that encode cellular tumor associated antigens include cellular oncogenes and proto-oncogenes that are aberrantly expressed. In general, cellular oncogenes encode products that are directly relevant to the transformation of the cell, and because of this, these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

Exemplary oncogenes that can be targeted to direct the disclosed compositions to tumors, tumor cells, or tumor microenvironments include, but are not limited to ABL1, ABL2, AKT1, AKT2, ATF1, BCL11A, BCL2, BCL3, BCL6, BCR, BRAF, CARD11, CBLB, CBLC, CCND1, CCND2, CCND3, CDX2, CTNNB1, DDB2, DDIT3, DDX6, DEK, EGFR, ELK4, ERBB2, ETV4, ETV6, EVI1, EWSR1, FEV, FGFR1, FGFR1OP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, MLL, TLX1, TPR, and USP6.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.,* 309:883 (1983); Lloyd, et al., *Int. J. Canc.,* 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.,* 36:755 (1997); Sarandakou, et al., *Eur. J. Gynaecol. Oncol.,* 19:73 (1998); Meier, et al., *Anticancer Res.,* 17(4B):2945 (1997); Kudoh, et al., *Gynecol. Obstet. Invest.,* 47:52 (1999)). Elevated serum CA125 may also accompany neuroblastoma (e.g., Hirokawa, et al., *Surg. Today,* 28:349 (1998), while elevated CEA and SCC, among others, may accompany colorectal cancer (Gebauer, et al., *Anticancer Res.,* 17(4B):2939 (1997)).

The tumor associated antigen, mesothelin, defined by reactivity with monoclonal antibody K-1, is present on a majority of squamous cell carcinomas including epithelial ovarian, cervical, and esophageal tumors, and on mesotheliomas. Using MAb K-1, mesothelin is detectable only as a cell-associated tumor marker and has not been found in soluble form in serum from ovarian cancer patients, or in medium conditioned by OVCAR-3 cells. Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies.

A tumor antigen may include a cell surface molecule. Tumor antigens of known structure and having a known or described function, include the following cell surface receptors: HER1 (GenBank Accession No. U48722), HER2 (GenBank Acc. Nos. X03363 and M17730), HER3 (GenBank Acc. Nos. U29339 and M34309), HER4 (GenBank Acc. Nos. L07868 and T64105), epidermal growth factor receptor (EGFR) (GenBank Acc. Nos. U48722, and K03193), vascular endothelial cell growth factor (GenBank No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043), insulin-like growth factor-II (GenBank Acc. Nos. X03562, X00910, M17863 and M17862), transferrin receptor (Trowbridge and Omary, Proc. Nat. Acad. USA, 78:3039 (1981); GenBank Acc. Nos. X01060 and Ml 1507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., Proc. Nat. Acad. Sci. USA, 86:7159 (1989); GenBank Acc. Nos. M65132 and M64928) NY-ESO-1 (GenBank Acc. Nos. AJ003149 and U87459), NA 17-A, Melan-A/MART-1 GenBank Acc. Nos. U06654 and U06452), tyrosinase (GenBank Acc. No. M26729), Gp-100 (GenBank Acc. No. S73003), MAGE (GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. No. U19180), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA; GenBank Acc. Nos. M59710, M59255 and M29540), and PyLT (GenBank Acc. Nos. J02289 and J02038); p97 (melanotransferrin), Additional tumor associated antigens include prostate surface antigen (PSA); β-human chorionic gonadotropin (β-HCG); glycosyltransferase β-1,4-N-acetylgalactosaminyltransferases (GalNAc); NUC18; melanoma antigen gp75 (GenBank Accession No. X51455); human cytokeratin 8; high molecular weight melanoma antigen.

Tumor antigens of interest include antigens regarded in the art as "cancer/testis" (CT) antigens that are immunogenic in subjects having a malignant condition. CT antigens include at least 19 different families of antigens that contain one or more members and that are capable of inducing an immune response, including but not limited to MAGEA (CT1); BAGE (CT2); MAGEB (CT3); GAGE (CT4); SSX (CT5); NY-ESO-1 (CT6); MAGEC (CT7); SYCP1 (CT8); SPANXBI (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but are not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the disclosed fusion proteins.

b. Tumor Neovasculature Antigens

The targeted antigen may be specific to tumor neovasculature or may be expressed at a higher level in tumor neovasculature when compared to normal vasculature. Exemplary antigens that are over-expressed by tumor-associated neovasculature as compared to normal vasculature include, but are not limited to, VEGF/KDR, Tie2, vascular cell adhesion molecule (VCAM), endoglin and $\alpha_5\beta_3$ integrin/vitronectin. Other antigens that are over-expressed by tumor-associated neovasculature as compared to normal vasculature are known to those of skill in the art and are suitable for targeting by the disclosed fusion proteins.

2. Chemokine or Chemokine Receptors

In another embodiment, the bispecific aptamer specifically binds to one or more chemokine or a chemokine receptor. Chemokines are soluble, small molecular weight (8-14 kDa) proteins that bind to their cognate G-protein coupled receptors (GPCRs) to elicit a cellular response, usually directional migration or chemotaxis. Tumor cells secrete and respond to chemokines, which facilitate growth that is achieved by increased endothelial cell recruitment and angiogenesis, subversion of immunological surveillance and maneuvering of the tumoral leukocyte profile to skew it such that the chemokine release enables the tumor growth and metastasis to distant sites. Thus, chemokines are important for tumor progression.

Based on the positioning of the conserved two N-terminal cysteine residues of the chemokines, they are classified into four groups namely CXC, CC, CX3C and C chemokines. The CXC chemokines can be further classified into ELR+ and ELR− chemokines based on the presence or absence of the motif 'glu-leu-arg (ELR motif)' preceding the CXC sequence. The CXC chemokines bind to and activate their cognate chemokine receptors on neutrophils, lymphocytes, endothelial and epithelial cells. The CC chemokines act on several subsets of dendritic cells, lymphocytes, macrophages, eosinophils, natural killer cells but do not stimulate neutrophils as they lack CC chemokine receptors except murine neutrophils. There are approximately 50 chemokines and only 20 chemokine receptors, thus there is considerable redundancy in this system of ligand/receptor interaction.

Chemokines elaborated from the tumor and the stromal cells bind to the chemokine receptors present on the tumor and the stromal cells. The autocrine loop of the tumor cells and the paracrine stimulatory loop between the tumor and the stromal cells facilitate the progression of the tumor.

Notably, CXCR2, CXCR4, CCR2 and CCR7 play major roles in tumorigenesis and metastasis. CXCR2 plays a vital role in angiogenesis and CCR2 plays a role in the recruitment of macrophages into the tumor microenvironment. CCR7 is involved in metastasis of the tumor cells into the sentinel lymph nodes as the lymph nodes have the ligand for CCR7, CCL21. CXCR4 is mainly involved in the metastatic spread of a wide variety of tumors.

In one embodiment, tumor or tumor-associated neovasculature targeting domains are ligands that bind to cell surface antigens or receptors that are specifically expressed on tumor cells or tumor-associated neovasculature or are overexpressed on tumor cells or tumor-associated neovasculature as compared to normal tissue. Tumors also secrete a large number of ligands into the tumor microenvironment that affect tumor growth and development. Receptors that bind to ligands secreted by tumors, including, but not limited to growth factors, cytokines and chemokines, including the chemokines provided above, are suitable for use in the disclosed fusion proteins. Ligands secreted by tumors can be targeted using soluble fragments of receptors that bind to the secreted ligands. Soluble receptor fragments are fragments polypeptides that may be shed, secreted or otherwise extracted from the producing cells and include the entire extracellular domain, or fragments thereof.

In another embodiment the aptamers of the disclosed compositions specifically bind to one or more target antigens selected from the group consisting of carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1α, AFP, PSMA, CEACAM5, CEACAM6, c-met, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PIGF, complement factors C3, C3a, C3b, C5a, C5, PLAGL2, and an oncogene product. A particularly preferred target antigen is CEACAM5 (CEA).

3. Viral Antigens

In some embodiments, the protein that is bound by the aptamer is one or more viral proteins selected from the group consisting of a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

One embodiment provides a bispecific aptamer that binds one or more of Alpha-fetoprotein (AFP), Beta-2-microglobulin (B2M), Beta-human chorionic gonadotropin (Beta-hCG), C-kit/CD117, CA15-3/CA27.29, CA 125, CA 19-9, Calcitonin, Carcinoembryonic antigen (CEA), CD20, Chromogranin A (CgA), Cytokeratin fragment 21-1, HE4, Neuron-specific enolase (NSE), Programmed death ligand 1 (PD-L1), Prostate-specific antigen (PSA), Thyroglobulin, Epithelial tumor antigen (ETA), Melanoma-associated antigen (MAGE), MUC-1, CD44, EpCAM and combinations thereof.

B. EpCAM

A preferred binding target is epithelial cell adhesion molecules (EpCAM), a glycosylated membrane protein, is overexpressed in over 70% of OC and its level is closely associated with malignant ascites, chemoresistance, and decreased survival rate in OC patients (Tsikouras, et al, *Arch Gynecol Obstet*, 288:581-585 (2013)). Although normal epithelial tissues usually express EpCAM, its expression in the peritoneal cavity appears to be tumor specific because mesothelial cells in the abdominal cavity are negative for EpCAM expression (Blazar, et al., *J Mol Med* (Berl), 77:699-712 (1999); Reichert, et al., *Net Rev Drug Discov.*, 6:349-356 (2007)). Since downregulation of EpCAM inhibits cell-cell adhesion and epithelial-mesenchymal transition, it has been postulated that EpCAM participates in ovarian cancer progression by regulating the process of EMT (Baeuerle, et al., *Br J Cancer*, 96:417-423 (2007)). In addition, EpCAM-associated oncogenic features have recently also been connected to the enhanced transcription of c-Myc and the cyclin A/E (Reichert, et al., *Net Rev Drug Discov.*, 6:349-356 (2007). Moreover, EpCAM positive cells are well recognized to possess tumor-initiating potential and EpCAM has thus been used as a key marker of ovarian cancer stem cells (Imrich, et al., *Cell Adh Migr,* 6:30-38 (2012)). These findings strongly support the notion that EpCAM is an ideal therapeutic target for OC. Various EpCAM antagonists have been developed (Nunna, et al., *PLOS One,* 9:e87703 (2014)); in fact, EpCAM-targeted antibodies have demonstrated the treatment efficacy in both experimental models and clinical trials. For instance, EpCAM antibody MT20 was able to effectively eliminate ovarian cancer cells in preclinical model (Xiang, et al., *J Cancer Res Clin Oncol,* 129_341-348 (2003)) while treatment of EpCAM/CD3-bispecific antibody (Catumaxomab) led to substantial decrease of malignant ascites in OC patients (Burges, et al., *Clin Cancer Res,* 13:3899-3905 (2007)).

C. CD44

In addition to EpCAM, CD44 has been identified as another important molecule in OC progression that can be specifically bound by the bispecific aptamers (Wang et al., *Int J Mol Sci,* 16:3391-3404 (2015)). CD44 can organize a signaling platform which facilitates ovarian cancer cell growth, survival and metastasis (Orian-Rousseau, Frontiers in Immunology (2015)). CD44 can also serve as a receptor to mediate the attachment of ovarian cancer cells onto the peritoneal mesothelium by binding to mesothelium-associated hyaluronic acid (HA) (Gardner, et al., *Clin Exp Metastasis,* 14:325-334 (1996)). A recent study revealed that population of CD44+/CD24− ovarian cancer cells were chemoresistant (Wang et al., *Int J Mol Sci,* 16:3391-3404 (2015)). Analyses of ovarian cancer patient specimens further show that CD44 expression is associated with high-grade and advanced stage ovarian carcinoma (Zhang, et al., *Human Pathology,* 44:1882-1889 (2013)). These evidences clearly pinpoint a critical role of CD44 in ovarian cancer progression and metastasis (Sacks, et al., *Biomolecules,* 5:3051-3066 (2015)). This notion is buttressed by the observations that CD44-targeted antibodies or short hairpin RNAs inhibit ovarian cancer cell adhesion to mesothelial cells and peritoneal implantation (Strobel et al., *Cancer Res*, 57:1228-1232 (1997); Zou et al., *Neoplasma*, 61:274-282 (2014)).

V. Methods of Use

The disclosed bispecific aptamers can be used to inhibit tumor growth, treat cancer, or kill targeted cells.

A. Cancer

In one embodiment, the bispecific aptamers are administered to a subject having or suspected of having cancer in an amount effective to inhibit or reduce tumor growth and/or tumor burden. For example, the divalent siRNA chimera can have two aptamers that specifically bind to two different cancer antigens or tumor specific antigens or combinations of cancer antigens, tumor specific antigens, and tumor markers.

The genes to be down-regulated in the cancer or tumor cell are typically oncogenes or proto-oncogenes. Representative oncogenes to be targeted are selected from the group consisting of ABL1, ABL2, AKT1, AKT2, ATF1, BCL11A, BCL2, BCL3, BCL6, BCR, BRAF, CARD 11, CBLB, CBLC, CCND1, CCND2, CCND3, CDX2, CTNNB1, DDB2, DDIT3, DDX6, DEK, ELK4, ERBB2, ETV4, ETV6, EVI1, EWSR1, FEV, FGFR1, FGFR1OP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, MLL, TLX1, TPR, and USP6 is also down-regulated.

Thus, methods for treating cancer are provided. Cancers that can be treated include, but are not limited to ovarian cancer, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer such as but not limited to papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers including, but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including, but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or ureter); Wilms' tumor; bladder cancers including, but not limited to, transitional cell carcinoma, squamous cell cancer, adenocarcinoma, carcinosarcoma. Cancers that can be prevented, treated or otherwise diminished by the MDNPs include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, papillary adenocarcinomas, and gastric cancer.

B. Tumor Burden

Another embodiment provides a method for reducing the tumor burden of a subject by administering an effective amount of the bispecific aptamers that specifically binds at least two tumor specific antigen produced by the tumor.

C. Viral Infections

Another embodiment provides a method for treating a viral infection in a subject in need thereof by administering an effective amount of bispecific aptamers that specifically bind to viral proteins expressed on the surface of virally infected cells.

Exemplary viruses that can be treated include, but are not limited to pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, and hepatitis E virus.

D. Co-Therapies

The bispecific aptamers can be used in combination or alternation with a second therapeutic.

1. Cancer Co-Therapies

Non-limiting examples of one or more other therapies that can be used in combination with the bispecific aptamers include immunomodulatory agents, such as but not limited to, chemotherapeutic agents and non-chemotherapeutic immunomodulatory agents. Non-limiting examples of chemotherapeutic agents include cyclophosphamide, methotrexate, cyclosporin A, leflunomide, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan. Examples of non-chemotherapeutic immunomodulatory agents include, but are not limited to, anti-T cell receptor antibodies (e.g., anti-CD4 antibodies (e.g., cM-T412 (Boeringer), IDEC-CE9.1□ (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH I H (Ilex)), anti-CD2 antibodies (e.g., MEDI-507 (MedImmune, Inc., International Publication Nos. WO 02/098370 and WO 02/069904), anti-CDl1 a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-alpha antibodies, anti-IL-1alpha antibodies, anti-IL-6 antibodies, anti-IL-8 antibodies (e.g., ABX-TL-8 (Abgenix)), anti-IL-12 antibodies and anti-IL-23 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-alpha receptor or a fragment thereof, the extracellular domain of an IL-1 alpha receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, IL-23, INF-alpha, INF-beta, interferon (IFN)-alpha, IFN-beta, IFN-gamma, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-alpha antibodies, and anti-IFN-gamma antibodies), and antibodies that immunospecifically bind to tumor-associated antigens (e.g., Herceptin®). In certain embodiments, an immunomodulatory agent is an immunomodulatory agent other than a chemotherapeutic agent. In other embodiments an immunomodulatory agent is an immunomodulatory agent other than a cytokine or hemapoietic such as IL-1, IL-2, IL-4, IL-12, IL-15, TNF, IFN-alpha, IFN-beta, IFN-gamma, M-CSF, G-CSF, IL-3 or erythropoietin. In yet other embodiments, an immunomodulatory agent is an agent other than a chemotherapeutic agent and a cytokine or hemapoietic factor.

Non-limiting examples of anti-cancer agents that can be used as therapies in combination with the bispecific aptamers, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin 11, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimus tine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin;

zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-i; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanotcrone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In specific embodiments, an anti-cancer agent is not a chemotherapeutic agent.

2. Antiviral Co-Therapies

Antiviral agents that can be used in combination with bispecific aptamers include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination with bivalent siRNA chimeras include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oscltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

Materials and Methods

Materials. Cell culture media were purchased from Life technologies Corporation (Carlsbad, Calif.). Fetal bovine sera and Taq RNA polymerase were from Sigma-Aldrich (St Louis, Mo.). Antibodies were from Cell Signaling Technology (Danvers, Mass.). DuraScribe T7 Transcription kits were from Epicentre (Madison, Wis.). Recombinant human CD44 and EpCAM proteins were from Thermo Fisher Scientific. Alexa Fluor 488 Annexin V/Dead Cell apoptosis kits were from Invitrogen. ELISA Kits for detection of IFNα and TNFα were obtained from RayBiotech (Norcross, Ga.). TUNEL assay kits were purchased from R&D systems (Minneapolis, Minn.). CD44 siRNA and EpCAM siRNA were purchased from Life Technologies Corporation.

Cell lines. Cell lines including OVCAR8, SKOV3, OCC1, ES2 and HEK293 cells were purchased from the American Type Culture Collection (ATCC, Manassas, Va.). Luciferase stable OVCAR8 cell line was developed in house. OVCAR8 cells were transfected with PGL4.51[luc2/CMV/neo] plasmid (Promega) by Lipofectamine 3000 reagent (Invitrogen) following the manufacture procedures. After 72 h transfection, cells were selected by adding 400 µg/ml G418 antibiotic in DMEM containing 10% fetal bovine serum. After 1-month culture, luciferase activity in transfected cells was confirmed with One-Step Glow Assay kit (Fisher Scientific).

CD44-EpCAM construction. CD44 and EpCAM aptamers were individually synthesized by in vitro transcription with PCR products as templates. The CD44 aptamer ssDNA (5'-GGGATGGATCCAAGCTTACTGGCATCTGGAT-TGCGCGTGCCAGAATAAAGAGTATAACGTGT-GAATGGGAAGCTTCGATAGGAATTCGG) (SEQ ID NO:1) was synthesized from IDT as a PCR template. PCR was performed with forward primer (5'-TAATACGACTCACTATAGGGATGGATCCAAGC-TTACT-3') (SEQ ID NO:2) and reverse primer (5'-AATTT-CATCTCCTGAACAAGCTTTTCCGAAT-3') (SEQ ID NO:3). Forward primer contains T7 RNA polymerase promoter binding sequence which is underlined. Reverse primer contains adaptor sequence which is bolded. The ssDNA of EpCAM aptamer containing T7 RNA polymerase promoter site (underlined) and adaptor sequence (bolded) (5'-TAATACGACTCACTATGCGACTGGTTACCCGGT-CGTAAAATTTCATCTCCTGAACAAGCTT) (SEQ ID NO:4) was synthesized from IDT as a PCR template. PCR was performed with forward primer (5'-TAATACGACT-CACTATA GCGACTGGTTA-3) (SEQ ID NO:5) and reverse primer (5'-AAGCTTGTTCAGGA GATGA AATTT-TACGA-3') (SEQ ID NO:6). The PCR products were put into T-A cloning pCR 2.1 vector (Invitrogen) and sequenced. Transcription was performed with PCR product as templates using DuraScript transcription kits following manufacture's instruction. Two RNAs were mixed at molar ratio 1:1 and annealed to form one bispecific CD44-EpCAM molecule by heated at 94° C. for 3 min followed by slowly cooling to room temperature within 1 h.

Construction of controls without unpaired base linkers between aptamer and adaptor. For construction of CD44-EpCAM No linker control-1, the ssDNA of EpCAM aptamer is synthesized by IDT as PCR template with sequence of TAATACGACTCACTATGCGACTGGT-TACCCGGTCGTAAAATTTCATCTCCT-GAACAAGCTTTT (SEQ ID NO:7), which has two more "T" (underlined) at the 5'-termini compared with linker-containing EpCAM aptamer. For construction of CD44-EpCAM No linker control-2, the sequence of the ssDNA of EpCAM aptamer is TAATACGACTCAC-TATGCGACTGGTTACCCGGTCG(TAA)AATTT-CATCTCCTGAACAAGCTTTT (SEQ ID NO:8), which has been removed three base TAA (bolded) and added two more "T"s at the 5-termini of EpCAM aptamer compared with above linker-containing EpCAM aptamer. PCRs of two constructs were performed with forward primer (5'-TAATACGACTCACTATA GCGACTGGTTA-3') (SEQ ID NO:9) and reverse primer (5'-AAAAGCTTGTTCA GGAGATGAAATT-3') (SEQ ID NO:10) with each ssDNA template. Transcription was performed with PCR products as templates. EpCAM aptamers without linkers were individually annealed with CD44 aptamer to generate no linker controls: CD44-EpCAM No linker-1 without unpaired bases between CD44 aptamer and double stranded adaptor, and CD44-EpCAM No linker-2 without any unpaired bases between aptamers (CD44 or EpCAM) and double stranded adaptor.

Characterization of dual binding functionality of CD44-EpCAM. Serially diluted recombinant human CD44 protein (0-500 nM) was loaded into 96-well microtiter plates at 50

µg/well in triplicates and incubated overnight at 4° C. Plates were further blocked with 5% BSA/sperm DNA (500 µg/ml)/yeast tRNA (500 µg/ml)/0.05% Tween-20 in PBS/T buffer overnight. CD44-EpCAM conjugates or simply mixed CD44 and EpCAM aptamers were incubated with 1 µM recombinant human EpCAM for 4 h at room temperature. For simply mixed CD44 and EpCAM, prior putting CD44 and EpCAM aptamers together, CD44 aptamer was blocked with ssDNA (5'-AATTTCATCTCCTGAACAAGCTT-3') (SEQ ID NO: 11). After incubation, the mixtures of CD44-EpCAM aptamer and EpCAM protein, simply mixed CD44 aptamer plus EpCAM aptamer and EpCAM protein were added into CD44-immobilized plates and incubated at 4° C. for 24 h. After washing with 1×PBS/0.05% Tween-20 for 4 times, 100 µl anti-EpCAM antibody at 1:1000 dilution was added and incubated for 4 h at room temperature. After washing 4 times, 100 µl HRP-secondary antibody (1:5000) was added and incubated for 2 h at room temperature. Detection of HRP was performed by incubating with 100 µL/well soluble Turbo TMB-ELISA substrate for 5 min, then reaction was quenched with 100 µl/well Stop solution and the absorbance at 450 nm was measured using TECAN Infinite M 200 plate reader.

Serum stability assay. 2'-fluoro-modified and unmodified CD44-EpCAM (1 nmol) were incubated with final 50% human serum at 37° C. for 2 h, 6 h, and 24 h. RNA integrity was detected with 1% agarose gel electrophoresis in 1×TBE buffer. Aptamer intensity was measured with ImageJ (NIH).

Knockdown of CD44 and/or EpCAM. OVCAR8 cells were plated in 6-well plates at a density of 5×10 5 cells/well for 24 h. CD44 siRNA and/or EpCAM siRNA were transfected into cells using Lipofectamine RNAi MAX (Life Technologies) according to the manufacturer's instruction. Cells were harvested 72 h post-transfection and Western blot was performed to confirm gene knockdown. CD44 and/or EpCAM silenced cells were subjected to aptamer binding assay by BD FACSCalibur flow cytometry.

CD44-EpCAM aptamer binding specificity. OVCAR8, SKOV3, ES2, OCC1 and HEK293T cells were collected and washed with DPBS. OVCAR8 cells with CD44+(EpCAM silenced), EpCAM+ (CD44 silenced) and CD44− EpCAM− (both CD44 and EpCAM silenced) were collected after 72 h siRNA transfection. 3'-Cy5 labeled and 2'-fluoro-modified EpCAM (with adaptor) and MG aptamer were synthesized from TriLink. Cy5-labeled CD44-EpCAM was generated by annealing Cy5-EpCAM and CD44 aptamer through adaptor complementing. After washing, cells were incubated with Cy5-labeled CD44-EpCAM (1 µM) or Cy5-labeled MG aptamer (1 µM) in 1×TBS buffer containing 5% BSA, yeast tRNA (500 µg/ml), sperm DNA (500 µg/ml), and 0.05% Tween-20 for 1 h at 37° C. incubator. Cell binding was detected using BD FACSCalibur flow cytometry.

Western blot. Cells were lysed in lysis buffer (M-PER Mammalian Protein Extraction Reagent, Thermo Fisher Scientific) containing 1×Halt Protease Inhibitor Cocktails. After 2-h lysis and centrifuged at 12,000×g for 10 min at 4° C., cell supernatant was collected and the protein concentration was determined with Bio-Rad Protein Assay (Bio-Rad, Hercules, Calif.). Protein (100 µg) was mixed with 2× Laemmli sample buffer containing 5% β-mercaptoethanol and heated at 95° C. for 10 min. Denatured samples were separated on 10% SDS-polyacrylamide gel and transferred to PVDF membrane. The membranes were blocked with 5% non-fat milk overnight at 4° C., and then incubated with primary antibodies for 2 h at 4° C. overnight, followed by incubation with horseradish peroxidase-conjugated secondary antibodies for 2 h at room temperature. After ECL Western Blotting Substrate (Pierce) was added onto membrane, the signals were captured by the exposure to X-ray film.

Cell viability assay. Proliferation and cytotoxicity of CD44-EpCAM was quantified by measuring WST-8 formazan using Cell Counting Kit-8 (CCK-8) (Dojindo, Japan). Cells in Dulbecco's Modified Eagle Medium containing 10% fetal bovine serum were seeded in 96-well plate at a density of 1-5×103 in 5% $CO_2$ incubator for 24 h at 37° C. Cell lines of OVCAR8, SKOV3, OCC1, ES2 and HEK293T were incubated with the varying concentrations of aptamer constructs (CD44, EpCAM, CD44 plus EpCAM and CD44-EpCAM conjugate) for 72 hours. MG aptamer (specific to Malachite Green) (5'-GGAUCCCGACUGGCGAGAGCCAGGUAACGAAU GGAUCC-3') (SEQ ID NO:12) was used as an aptamer control. Absorbance was measured at 450 nm using a spectrophotometer.

Assessment of apoptosis and cell death by flow cytometry and fluorescent microscopy. OVCAR8 cells were treated with different concentrations of CD44-EpCAM for 48 h. The cells were harvested and stained with Alexa Fluor 488 Annexin V-Propidium Iodide (PI) solution for 15 min at room temperature. Apoptosis was detected by flow cytometry and fluorescent microscope. A portion of collected cells ($1×10^4$/sample) were acquired by BD FACSCalibur and analyzed using BD FACStation software, and another portion of collected cells were imaged with fluorescence microscopy (Nikon Eclipse TE2000-S). Each channel signals were separately captured and merged with ImageJ Plugin for co-localization.

Peritoneal metastatic assay. All animal studies were approved by the Institutional Animal Care and Use Committee at Augusta University. Athymic nu/nu female mice were purchased from Harlan Laboratories. The methods were carried out in accordance with the approved guidelines. Peritoneal metastatic colonization assays were performed as previously described [52, 53]. OVCAR8-luc cells ($5×10^6$) in the log phase were intraperitoneally injected into the mice. 5-day after implantation, mice were treated with PBS, CD44 aptamer, EpCAM aptamer, mixed CD44 and EpCAM aptamers, and CD44-EpCAM conjugate at 2 nmole per mouse every other day in the start two weeks and every day in the last two weeks. After 1-month treatment, luciferin was intraperitoneally injected to mice at 150 mg/kg. Before imaging, mice were anesthetized with isoflurane, bioluminescence imaging was performed with a Xenogen IVIS100 imaging system (Xenogen). Overall peritoneal metastasis was measured by selecting a region of interest (ROI) around the tumor sites of each mouse and quantified total flux using Living Image Software AMIVIEW 1.7.02 (Xenogen) with the units of photons/s/$cm^2$/sr.

Biodistribution assay. OVCAR8-luc cells (5×106) in the log phase were intraperitoneally injected into the mice. After 8-day implantation, mice were intraperitoneally injected with Cy5-labeled CD44-EpCAM aptamer (15 nmoles) or equal mole amount of Cy5-labeled MG aptamer (non-targeting control).The whole-body images were obtained at 0.5 h, 4 h and 8 h using Xenogen IVIS100 imaging system by setting wavelength at excitation 640 nm and emission 710 nm. After 8-h injection of Cy5-labeled aptamers, mice were intraperitoneally treated with luciferin at 150 mg/kg. Bioluminescence imaging was followed after Cy5 fluorescence imaging using Xenogen IVIS100. Mice were euthanized with $CO_2$ after whole-body imaging and organs (heart, lung, liver, spleen, kidney, muscle, brain, stomach, and intestine) were removed. The ex vivo images of Cy5

(aptamer) and bioluminescence (tumor cells) were captured at the same time using Xenogen IVIS100.

Histology assay. Mice were euthanized with $CO_2$, and tumors and organs (spleen, lung, kidney, intestine, heart, liver and muscle) were removed and fixed with 4% paraformaldehyde. Sections (6 μm) were cut and mounted on the slides, and deparaffinized in xylene and ethyl alcohol. Each block has a section for H&E staining. For immunohistochemistry assay, sections were incubated in 3% normal goat serum for 2 h and incubated with primary antibodies: caspase-3 (1:20), Ki67 (1:100), E-cadherin (1:100) and N-cadherin (1:100). After washing, the sections were incubated with biotinylated secondary antibody (1:200, VECTOR, Burlingame, Calif.) for 1 hour. Following washing, the sections were incubated with VECTASTAIN ABC reagents for 30 min. The images were captured with Nuance fluorescence microscope with bright field imaging system. TUNEL assay was performed according to the manufacturer's instruction. Paraffin embedded tissues were sectioned, dewaxed, hydrated and digested with Proteinase K. After washing, slides were immersed into quenching solution for 5 min, then incubated with TdT labeling buffer. After incubated with streptavidin-HRP for 10 min, following washing, DAB work solution was added into the slides. Then slides were counterstained with Methyl Green. The images were captured with Nuance fluorescence microscope.

Quantification of IHC staining. ImageJ and ImageJ plugin IHC profiler were applied for measurement. Images were changed to 8-bit grayscale type and inverted under "Edit" menu of ImageJ. After invert, the DAB stained areas are bright, and unstained areas are dark. The mean intensity was measured using "Measure" function under the "Analyze" menu of ImageJ. 8-10 fields of each treatment group were assessed. For TUNEL staining, before images were changed to greyscale, IHC profiler was used to do color deconvolution, by which DAB brown stain was separated from Methyl Green counterstain and then followed the same analysis as the above.

ELISA. Normal human peripheral blood mononuclear cells (PBMCs) were separated with BD Vacutainer cell preparation tubes with sodium citrate. Cells were seeded into 24-well plates at $10^6$/well for 24 h in RPMI medium containing 10% fetal bovine serum. CD44-EpCAM with the varying concentrations was added into cells, and cells were incubated for 24 h in 5% $CO_2$ incubator at 37° C. The cell culture supernatant was detected with human IFNα and TNFα ELISA kits following the manufacture's instruction. Statistical analysis. The Data were analyzed using two-tailed Student's t-test (Graph Pad Prism) by comparing with the control group, and expressed as a mean±SEM. The differences of $P<0.05$ was considered statistically significant.

Example 1: Construction and Characterization of a Bispecific CD44-EpCAM Aptamer

Single CD44 aptamer (Ababnem, et al., Nucleic Acid Ther, 23:401-407 (2013)) is 90 nucleotides long while single EpCAM aptamer (Shigdar, et al., Cancer Sci, 102:991-998 (2011)) is much smaller and contains only 19 nucleotides (FIG. 1A). The utilization of EpCAM aptamer is expected to confront with the problem of short circulation life time because molecular weight of 6.5 Kd of this aptamer is much smaller than the molecular mass cutoff of 30-50 Kd for renal glomerulus (Healy et al., Pharm Res, 21_2234-2246 (2004)). To overcome this problem, single CD44 and EpCAM aptamers were fused together with a 23 bp double stranded RNA adaptor. 2-3 bases were purposely left unpaired between adaptor and aptamer in order to give each single aptamer spatial space to form a 3-D structure shown in FIG. 1A. The molecular weight of fused aptamer is 54.4 Kd, which is large enough to avoid rapid renal depletion. The fused aptamer is much smaller than antibody, and thus expected to possess an ideal bioavailability to many biological compartments. To increase nuclease resistance, 2'-fluoro-pyrimidines were incorporated into the entire RNA during the process of in vitro transcription.

Figure 1B:
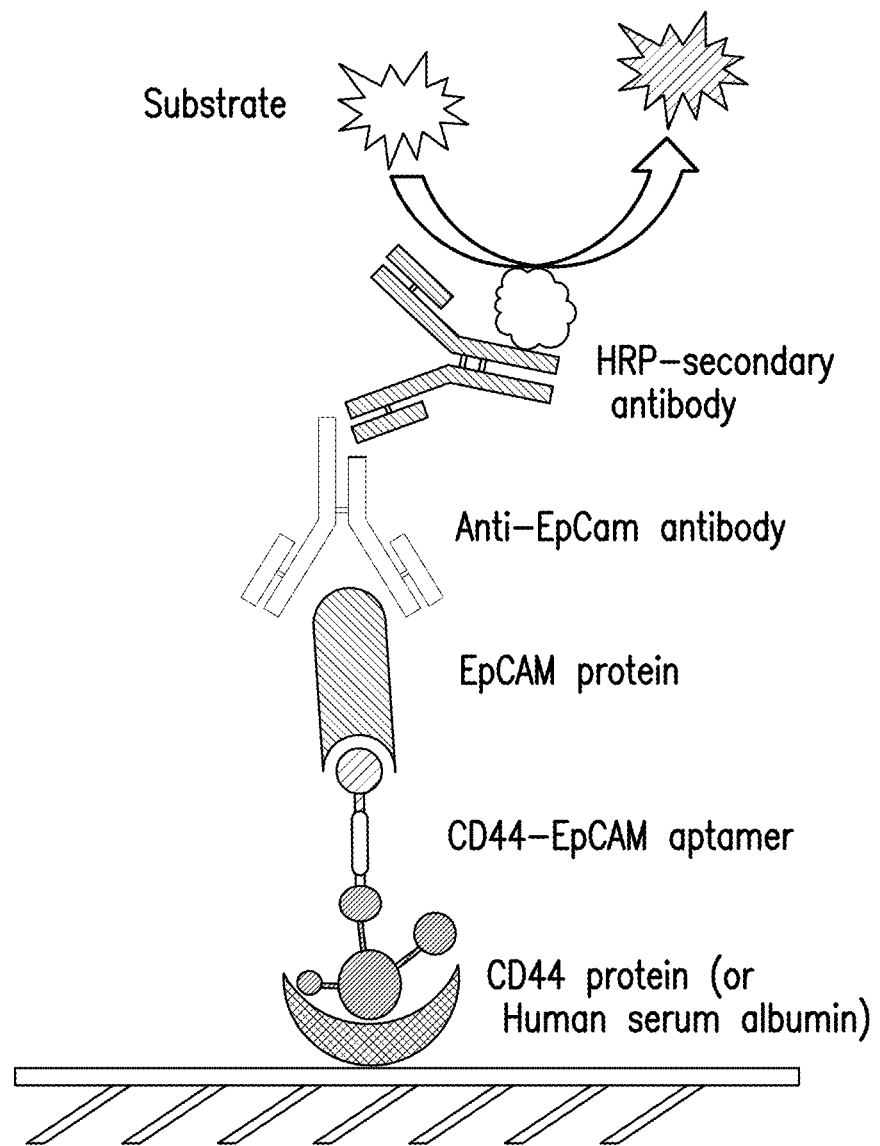
Figure 1C:
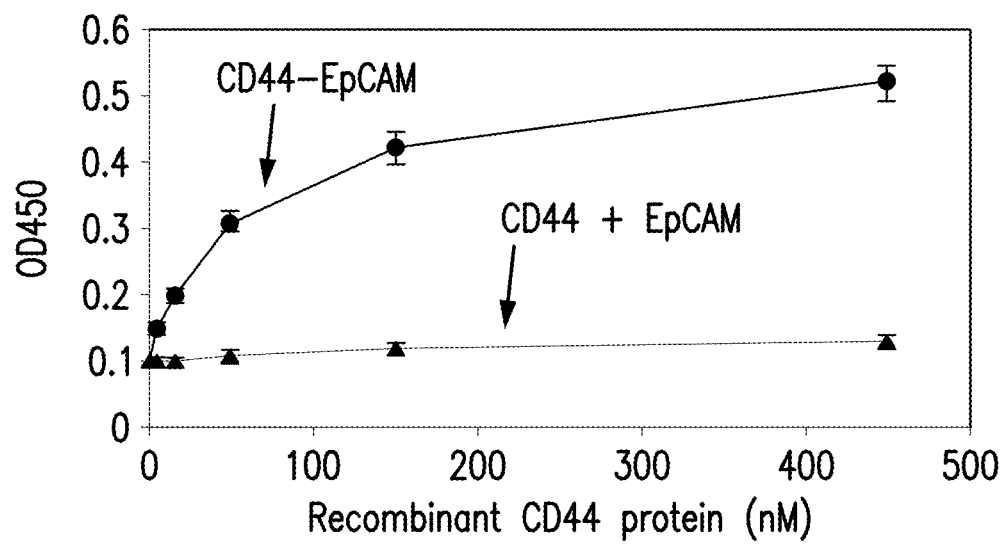
Figure 1D:
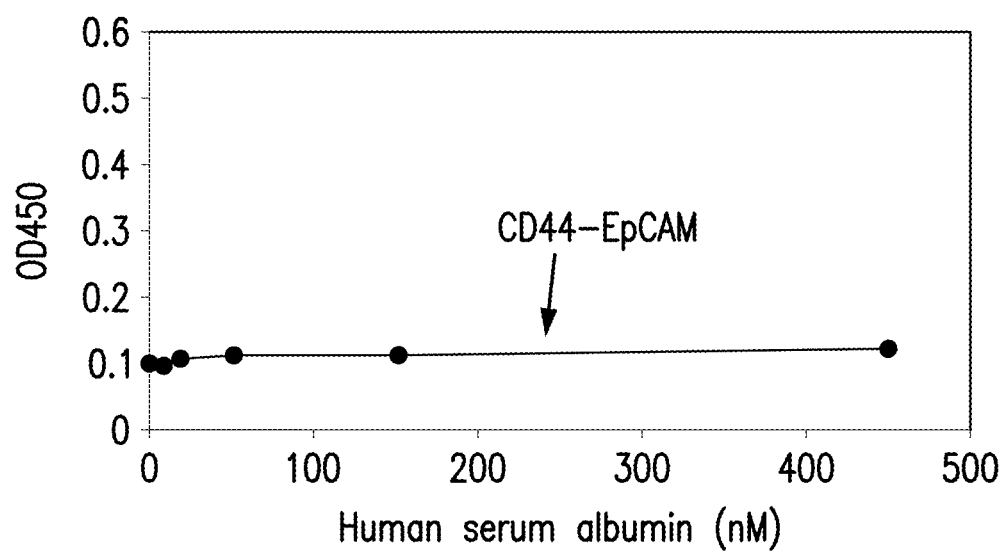

The binding of bispecific CD44-EpCAM aptamer was examined by ELISA (FIG. 1B). Serially diluted human recombinant CD44 protein was immobilized on a 96-well plate. Following CD44-EpCAM incubated with 1 μM EpCAM recombinant protein for 2 h, the incubation mixture containing CD44-EpCAM aptamer and EpCAM protein were added into CD44 protein-immobilized plate. Control is the simply mixed CD44 aptamer and EpCAM aptamer. After washing, anti-EpCAM antibody was added to the plates followed by HRP-secondary antibody. As expected (FIG. 1C), CD44-EpCAM bispecific aptamers successfully linked to plate-immobilized CD44 protein and free EpCAM proteins, yielding CD44 protein concentration-dependent positive signals, whereas only the background signal was detected in a control experiment with a simple mixture of CD44 aptamer and EpCAM aptamer. In another control experiment, human serum albumin (HSA) has been immobilized to the plates and detected with CD44-EpCAM, however, there is no positive signal detectable (FIG. 1D). These results suggest that bispecific CD44-EpCAM aptamer can efficiently bind both CD44 and EpCAM.

Figure 9A:
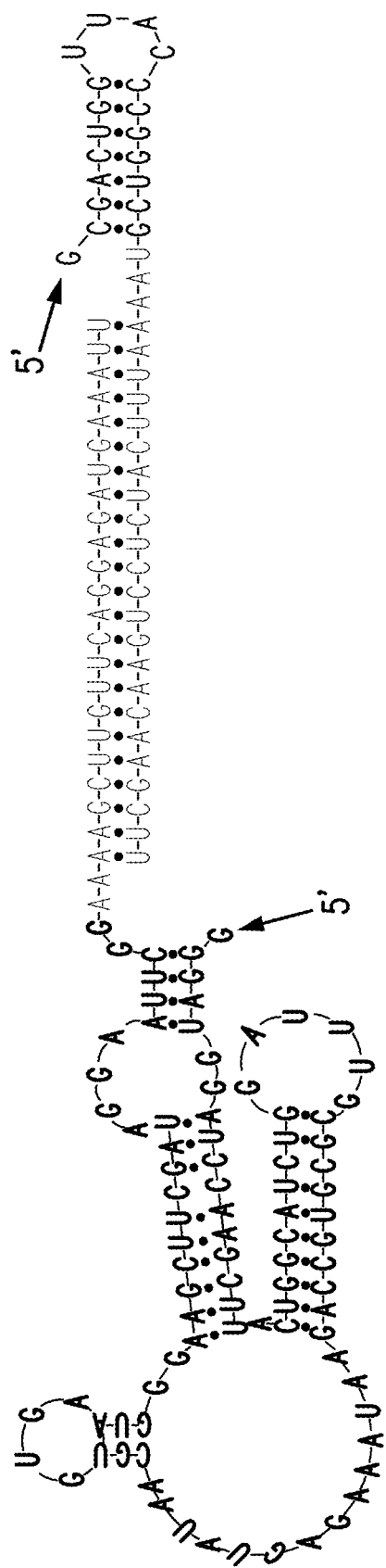
FIGS. 9A-9D. Effect of unpaired base linkers between aptamer and double stranded adaptor on activity of CD44-EpCAM aptamer.
Figure 9B:
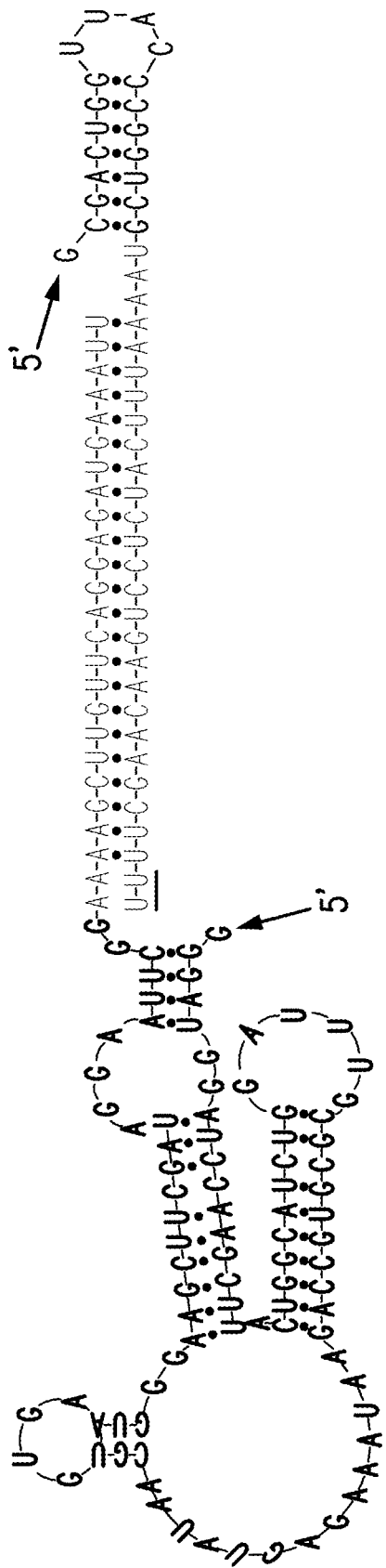
Figure 9C:
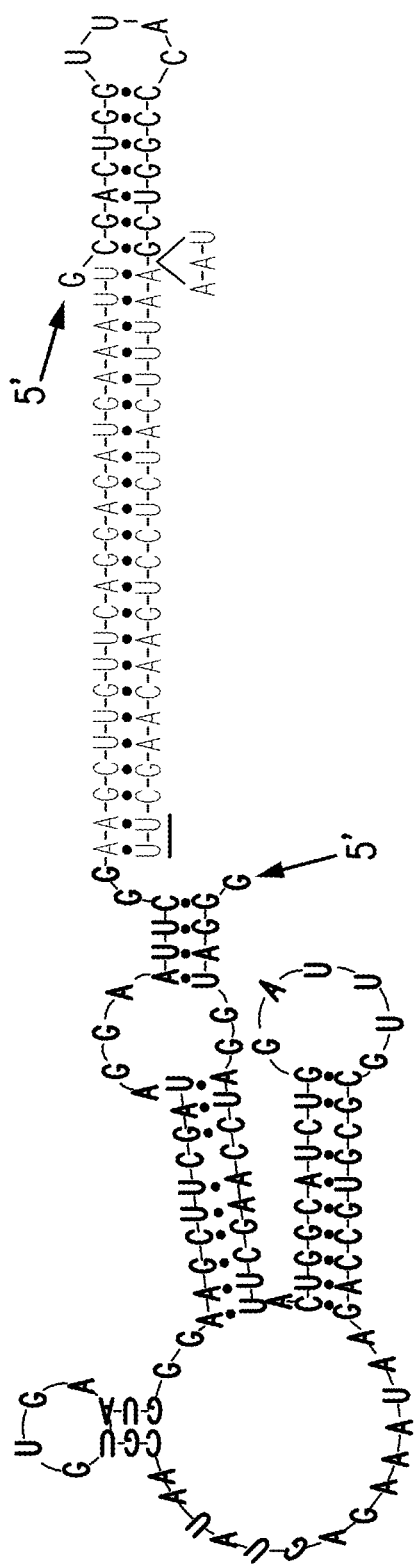
Figure 9D:
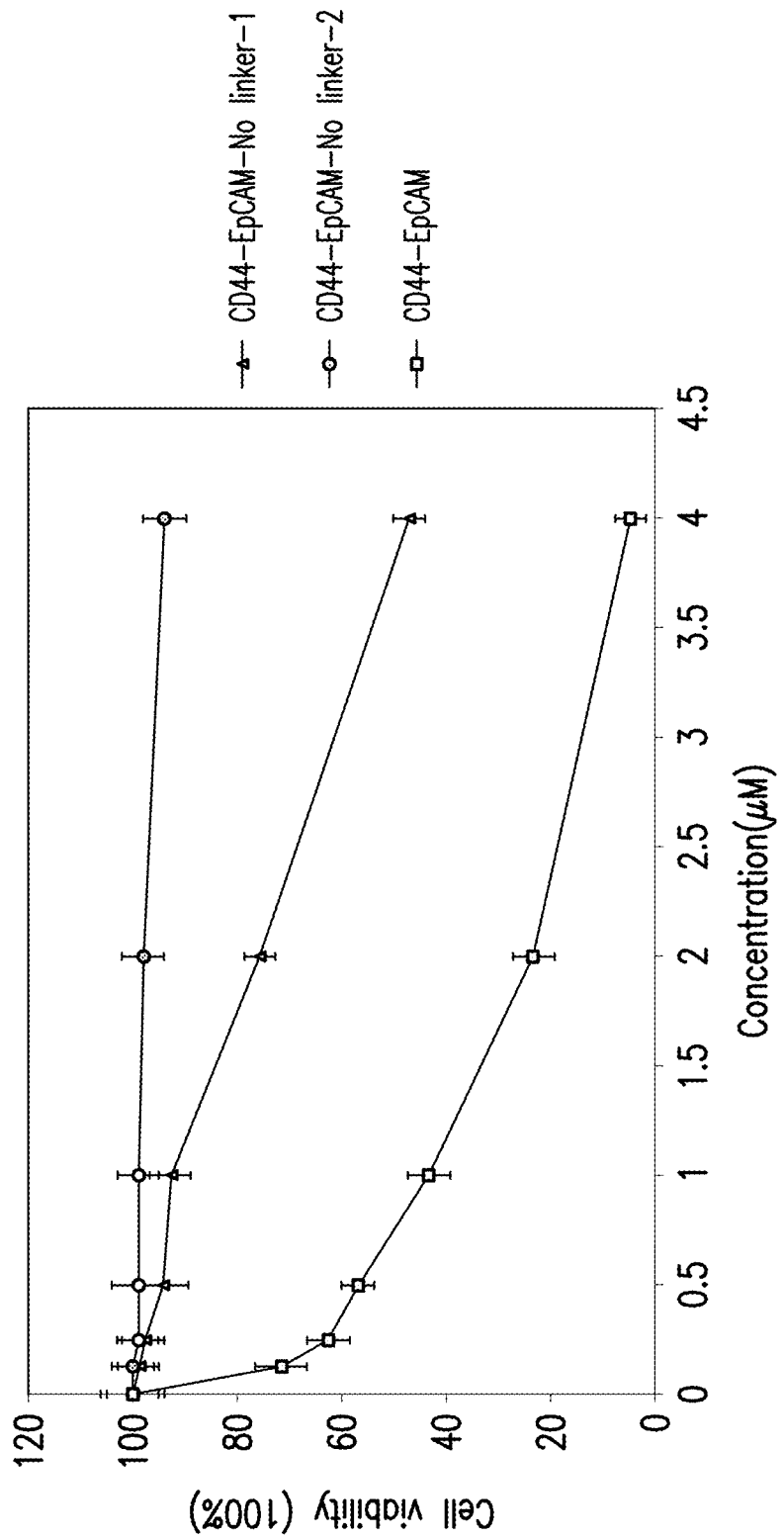
Figure 10:
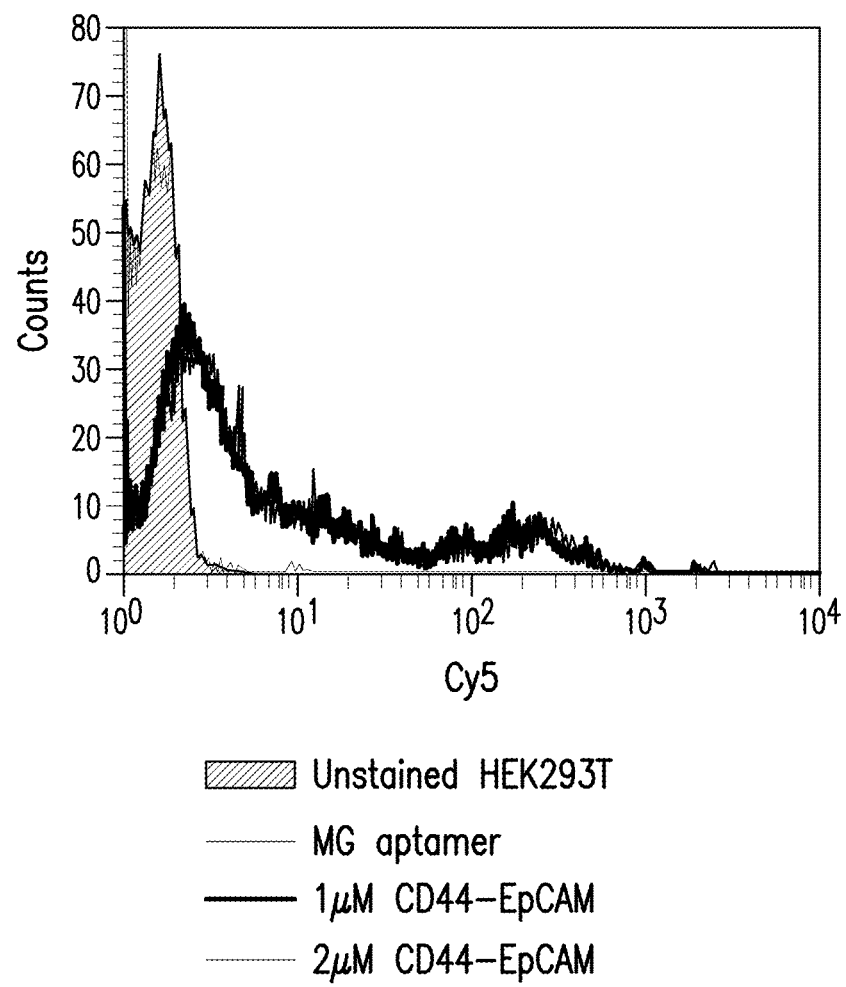
FIG. 10 shows the evaluation of nonspecific binding of CD44-EpCAM at the concentration of 2 μM. Histogram showing binding of CD44-EpCAM and HEK293T cells blocked with 500 g/ml sperm DNA, 500 μg/ml yeast tRNA and 5% bovine serum albumin in TBS/0.05% tween buffer.

To verify if the 2-3 unpaired bases (linkers) between double-stranded adaptor and aptamer are important in keeping functionality of two aptamers, two controls were constructed which contain no or only one unpaired linker (FIGS. 9A-9C). OVCAR8 cells were treated with linker-containing CD44-EpCAM and no linker controls. As shown in FIG. 9D, the control CD44-EpCAM No linker-1 (▲) which lacks the linker (unpaired two "A") between CD44 aptamer and adaptor showed 25% of cytotoxicity at 2 μM and 53% at 4 μM, in contrast, cytotoxicity of linker-containing CD44-EpCAM (■) is 77% at 2 μM and 95% at 4 μM. Moreover, the removal of all unpaired base linkers (CD44-EpCAM No linker-2; ●) has resulted about 95% activity loss (FIG. 9D). The results clearly demonstrate that 2-3 unpaired bases between aptamer and double stranded adaptor in this construct is crucial to render each aptamer function.

Figure 2A:
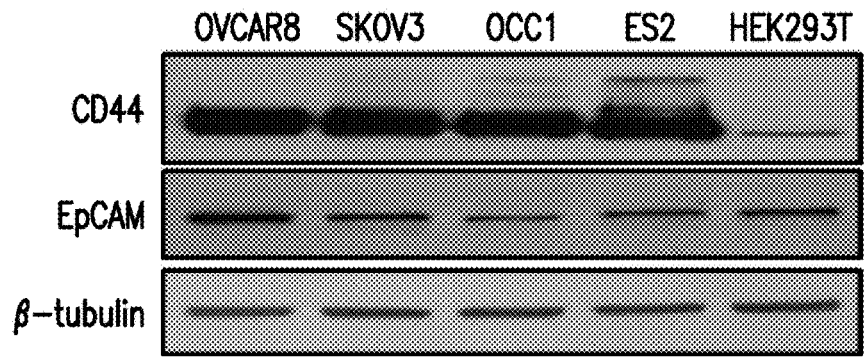
FIGS. 2A-2F show the evaluation of CD44 and EpCAM expression and cytotoxicity of CD44-EpCAM.
Figure 2B:
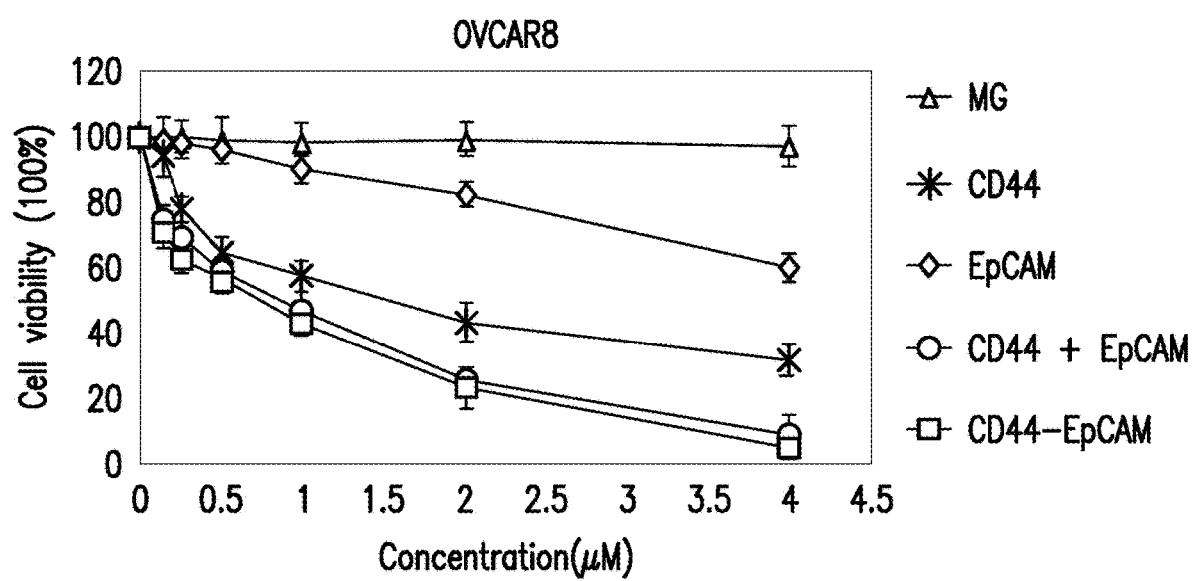
Figure 2C:
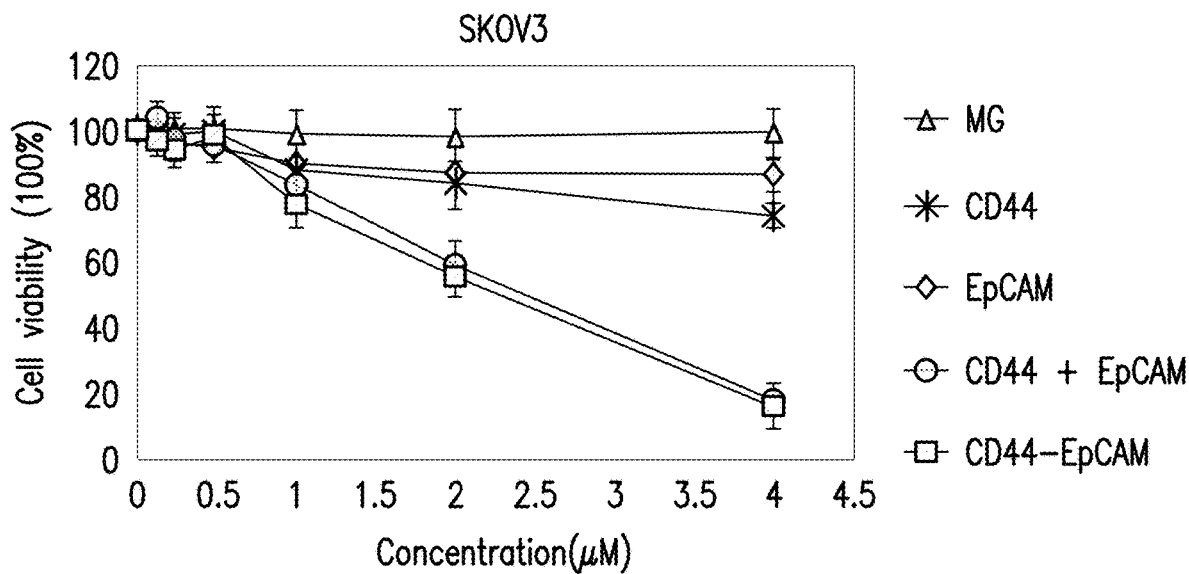
Figure 2D:
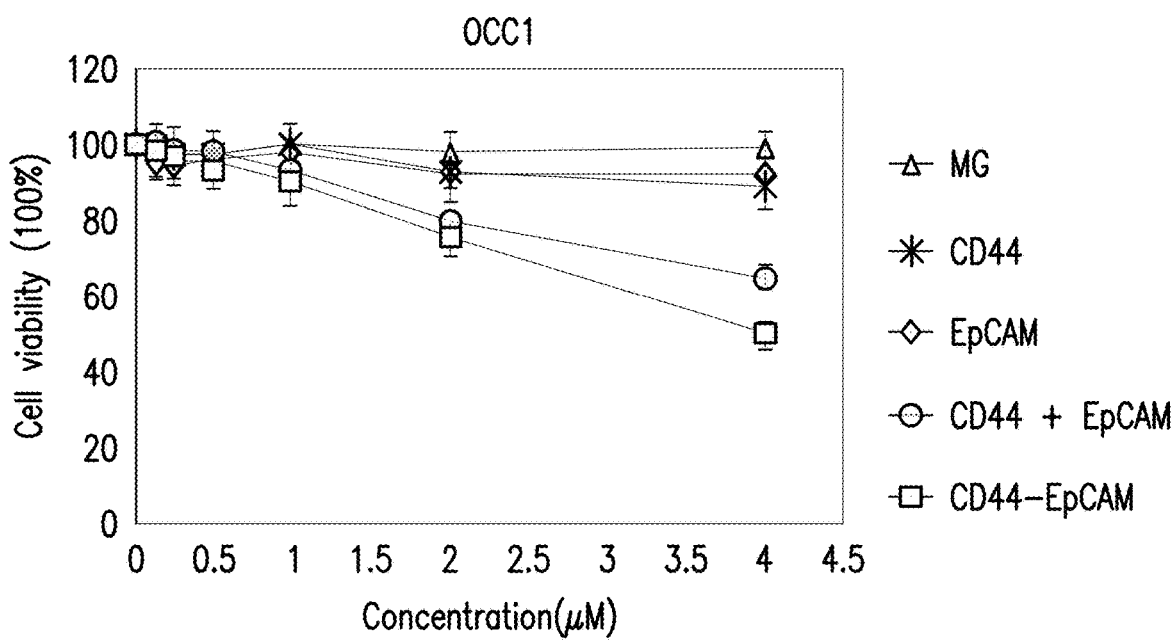
Figure 2E:
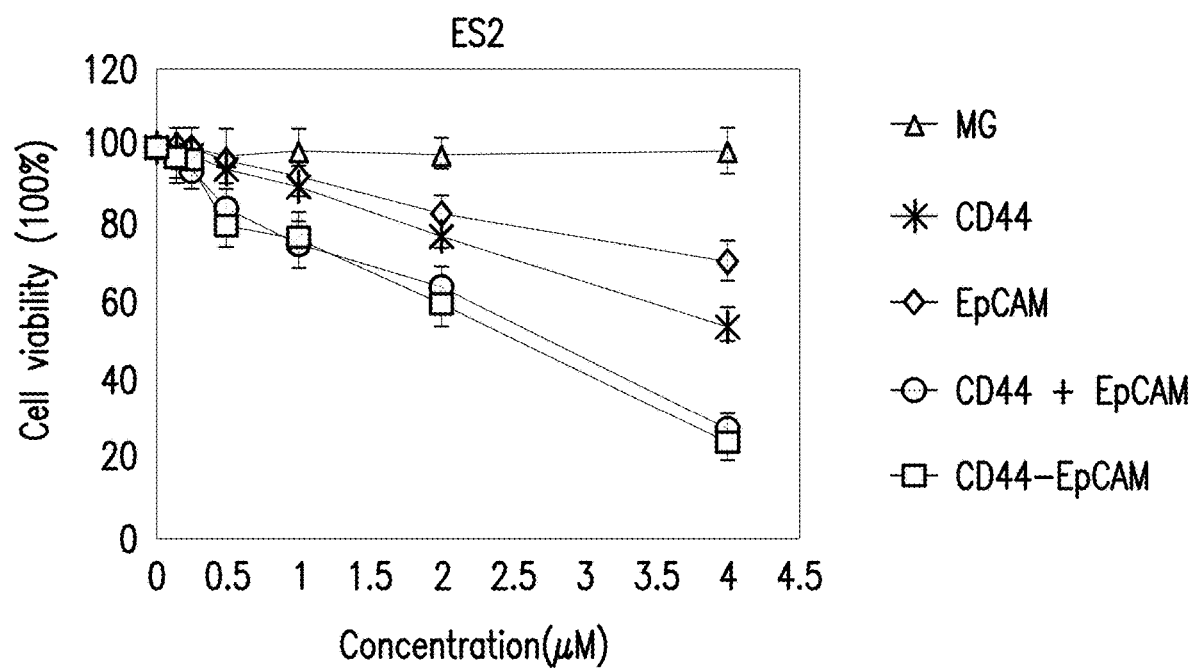

Example 2: The Expression of CD44 and EpCAM in Ovarian Cancer Cell Lines and Cytotoxicity of Bispecific CD44-EpCAM Aptamer To investigate the effect of bispecific CD44-EpCAM aptamer on ovarian cancer cell growth, the abundance of CD44 and EpCAM in a panel of ovarian cancer cell lines and human embryonic kidney HEK293T cell line was analyzed. Western blotting with the specific antibodies showed that CD44 was highly expressed in all ovarian cancer cell lines (OVCAR8, SKOV3, OCC1 and ES2) while little was seen in HEK293T cells (FIG. 2A). EpCAM was also expressed in all ovarian cancer cell lines and HEK293T cell line with highest expression detected in OVCAR8 cells (FIG. 2A).

Figure 2F:
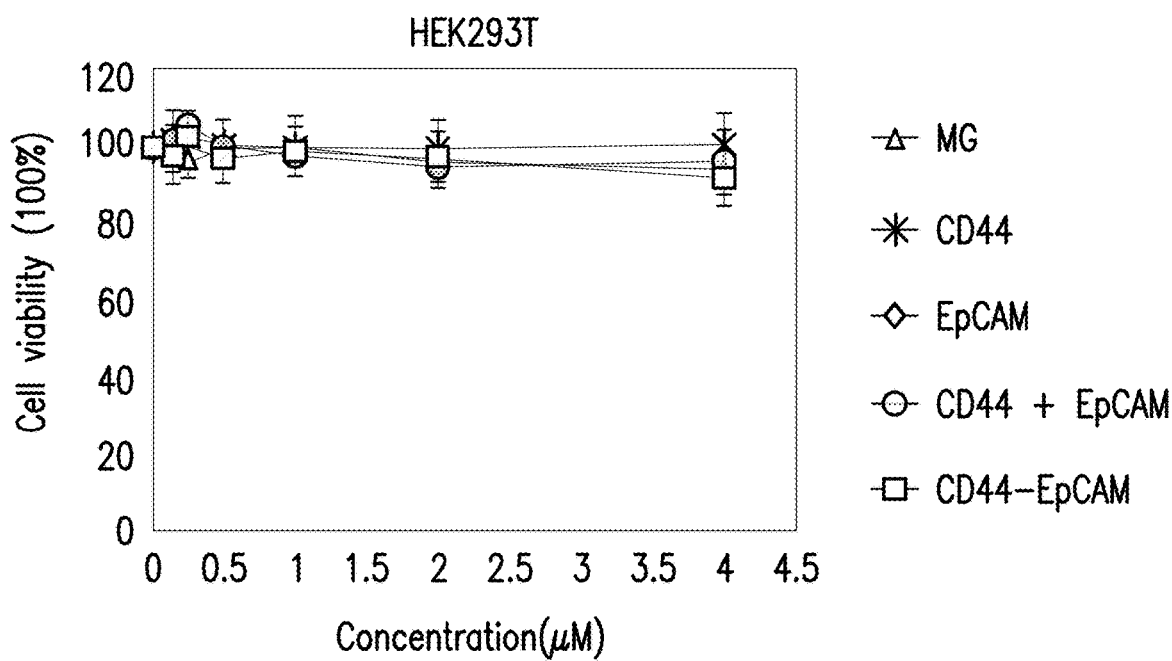

The cytotoxicity of both single and bispecific CD44 and EpCAM aptamers on ovarian cancer cells was assessed by CCK-8 assay. Single EpCAM aptamer displayed little inhibitory effect at concentration <2 μM but was able to reduce 10-30% of cell viability at 4 µM in tested ovarian cancer cell lines (FIGS. 2B-2E). In contrast, single CD44 aptamer dose-dependently reduced viability of OVCAR8 (FIG. 2B), ES2 (FIG. 2E), and SKOV3 (FIG. 2C) but not OCC1 (FIG. 2D) cells. Interestingly, bispecific CD44-EpCAM at 4 µM reduced viability of all four ovarian cancer cell lines with 95% reduction in OVCAR8, 92% in ES2, 84% in SKOV3 and 50% in OCC1 cells. Effect of CD44-EpCAM aptamer was clearly specific because MG aptamer (specific to Malachite Green) displayed no any cytotoxicity up to 4 µM in any of these cell lines. These results clearly demonstrate that bispecific CD44-EpCAM aptamer exhibits much greater potency in reducing ovarian cancer cell viability. Since none of the aptamer affected growth of HEK293T cells (FIG. 2F), these results indicate that bispecific CD44-EpCAM aptamer may specifically suppress ovarian cancer cell growth.

Example 3: Serum Stability of Bispecific CD44-EpCAM Aptamer

Figure 3A:
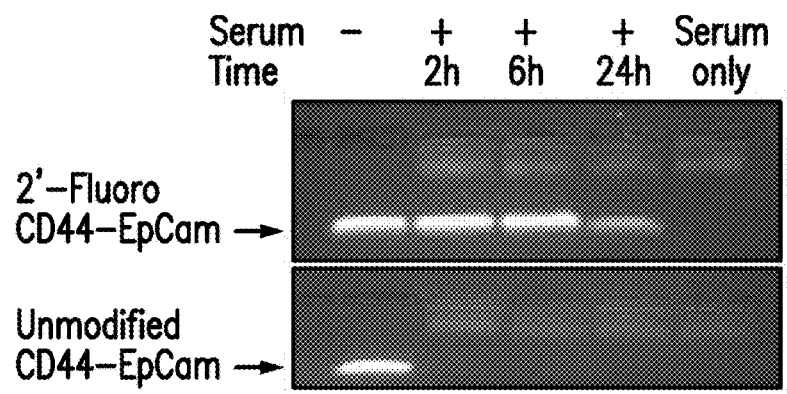
FIGS. 3A-3I show the evaluation of serum stability and binding specificity.
Figure 3B:
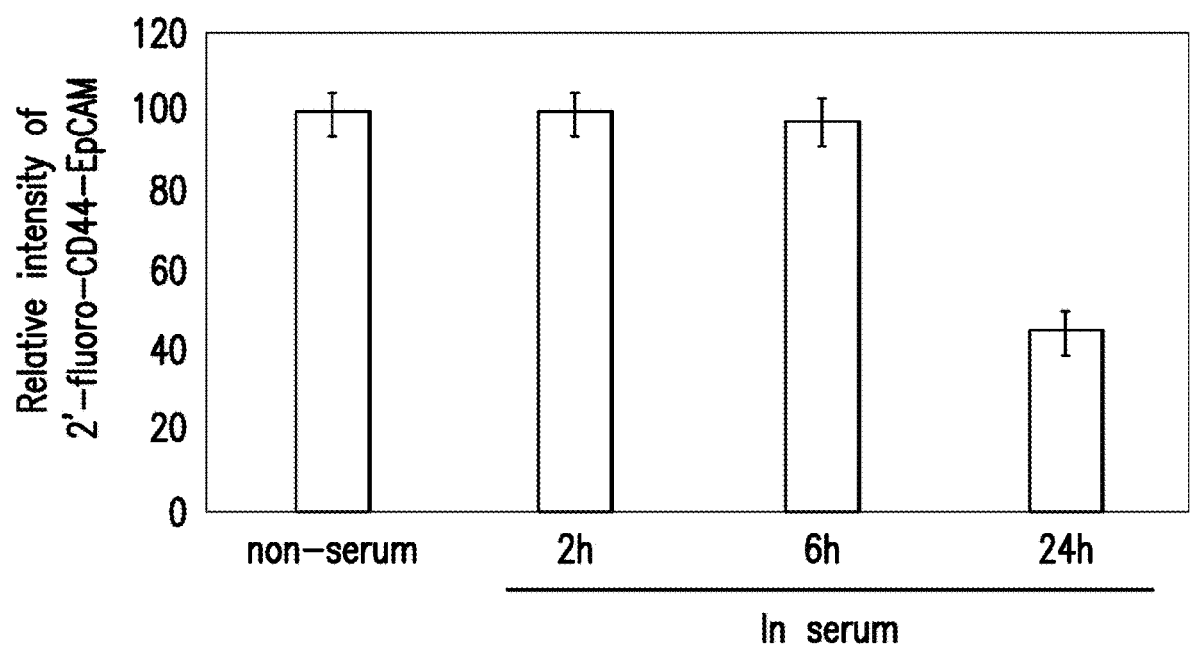
Figure 3C:
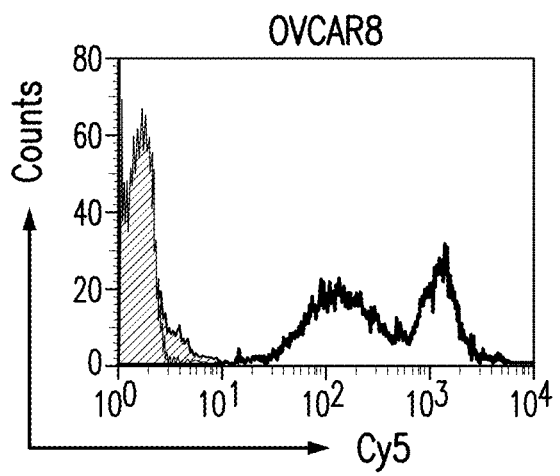
Figure 3D:
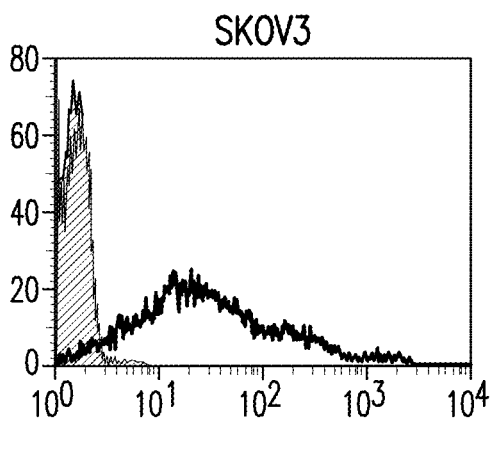
Figure 3E:
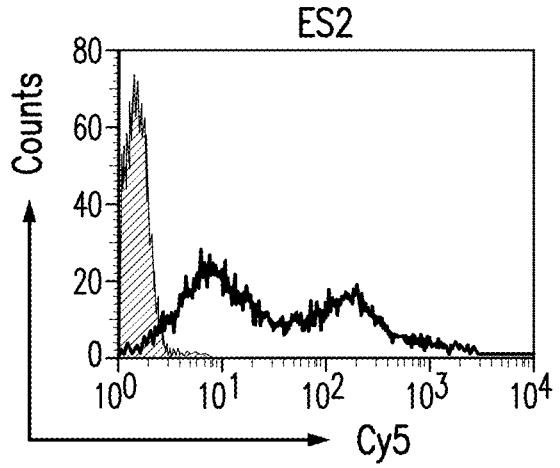
Figure 3F:
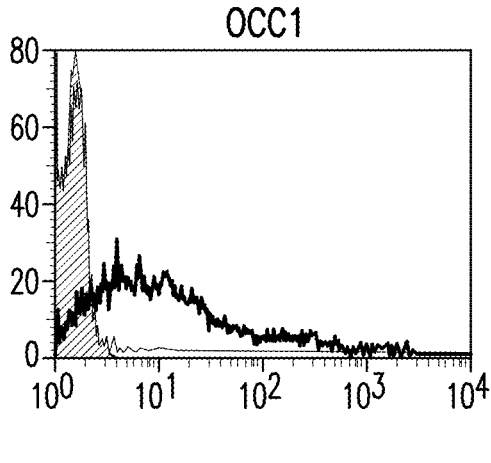
Figure 3G:
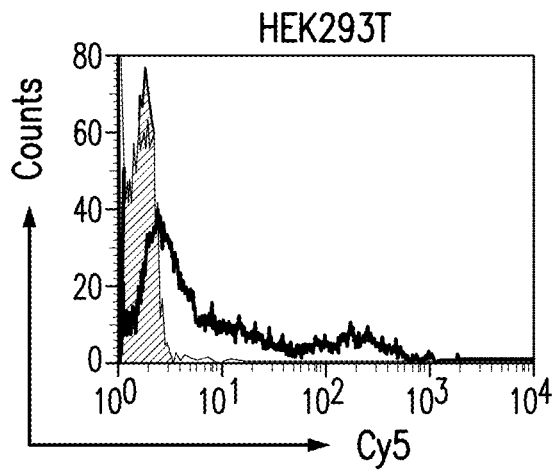

2'-fluoro-modified and unmodified CD44-EpCAM were incubated with 50% human serum at 37° C. for 2-24 h followed by agarose gel electrophoresis to reveal RNA integrity. As shown in FIGS. 3A & 3B, unmodified CD44-EpCAM was degraded as early as 2-h after treatment, and no aptamer bands appear in 24-h incubation time range. On the contrary, 2'-fluoro-modified CD44-EpCAM kept its integrity (tight band) without degradation for 6 h, and almost 45% of aptamer still remained at 24 h.

Example 4: Binding Specificity of Bispecific CD44-EpCAM Aptamer

Figure 3H:
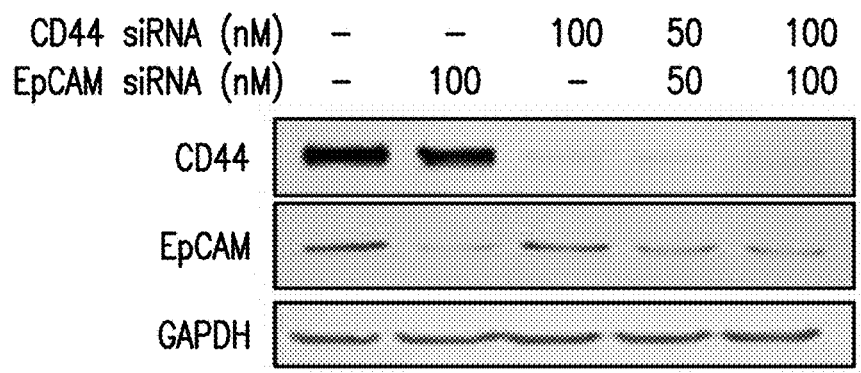
Figure 3I:
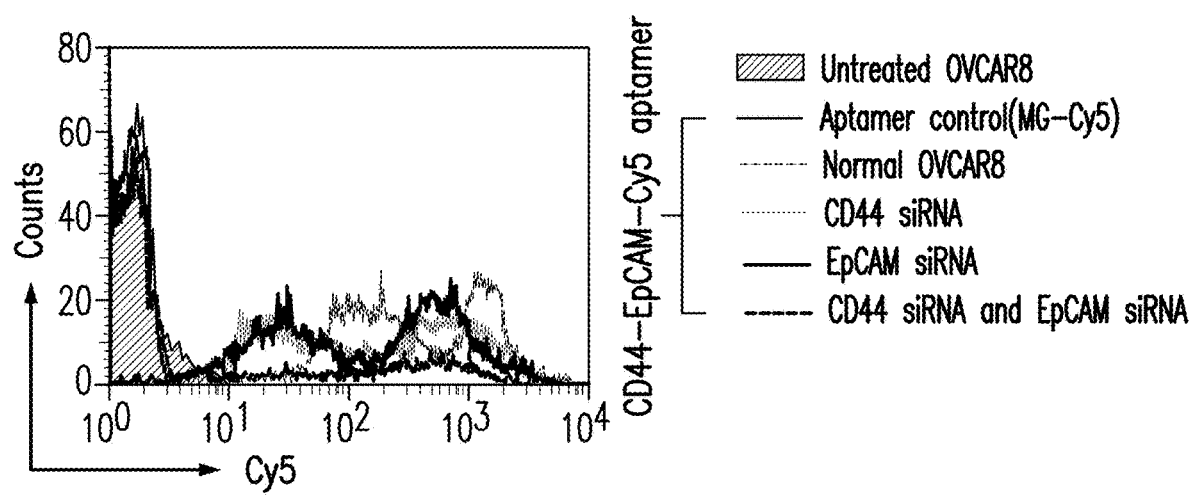

To confirm target specificity of CD44-EpCAM aptamer, the binding patterns of different cell lines stained with CD44-EpCAM was assessed with flow cytometry. EpCAM aptamer was labeled with Cy5 at its 3' end (TriLink), and CD44-EpCAM-Cy5 was generated by annealing equal moles of EpCAM-Cy5 with CD44 aptamer. As shown in FIGS. 3C-3G, OVCAR8, SKOV3 and ES2 show strong positive fluorescent intensity, and the intensity of OCC1 is weaker than OVCAR8, SKOV3 and ES2, but stronger than HEK293T. Whether the bispecific aptamer indeed binds to CD44 and EpCAM molecules was investigated further. CD44 and EpCAM on OVCAR8 cells were subjected to knockdown by siRNAs. CD44+(EpCAM silenced), EpCAM+(CD44 silenced), and CD44−EpCAM− (both CD44 and EpCAM silenced) cells were used for evaluation of target specificity. First, Western blot was performed to detect gene knockdown. As shown in FIG. 3H, by treatment with 100 nM of CD44 siRNA and/or EpCAM siRNA, OVCAR8 cells have significantly reduced protein levels of CD44 and/or EpCAM. Next, CD44+EpCAM+(no siRNA treatment), CD44+(EpCAM silenced), EpCAM+(CD44 silenced), and CD44− EpCAM− (both CD44 and EpCAM silenced) OVCAR 8 cells were stained with CD44-EpCAM-Cy5. As shown in FIG. 3I, CD44+EpCAM+OVCAR 8 cells (---) showed two strong fluorescence peaks and high fluorescence intensity, but after knockdown of CD44 or EpCAM, two fluorescence peaks of single positive CD44+ cells (-) or EpCAM+cells (-) significantly shift to left (lower intensity areas), which indicate reduced the binding. Upon knockdown of both CD44 and EpCAM, CD44-EpCAM-cells (---) lose the binding with CD44-EpCAM by exhibiting significantly reduced fluorescence intensity with near disappearance of two strong fluorescence peaks (FIG. 3I). The results demonstrated that the binding of CD44-EpCAM aptamer to cells is indeed through CD44 and EpCAM molecules.

Figure 4A:
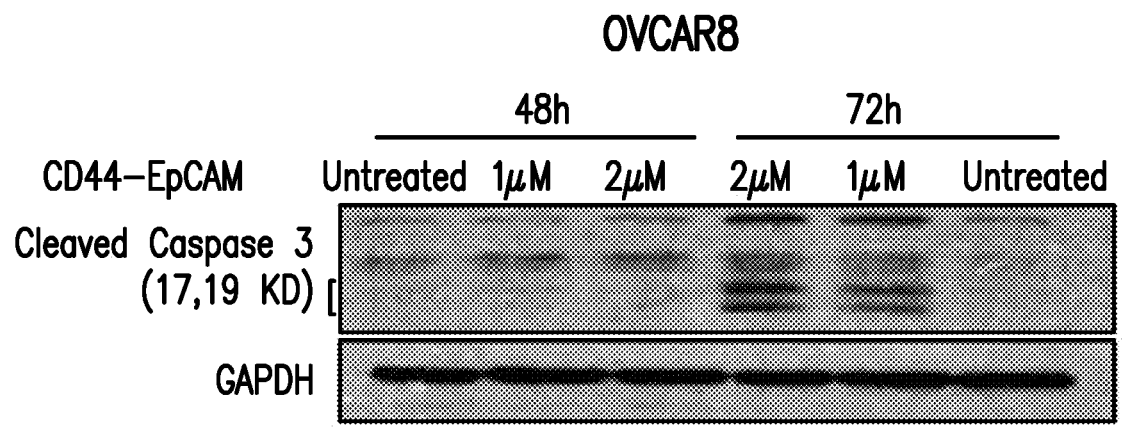
Figure 4B:
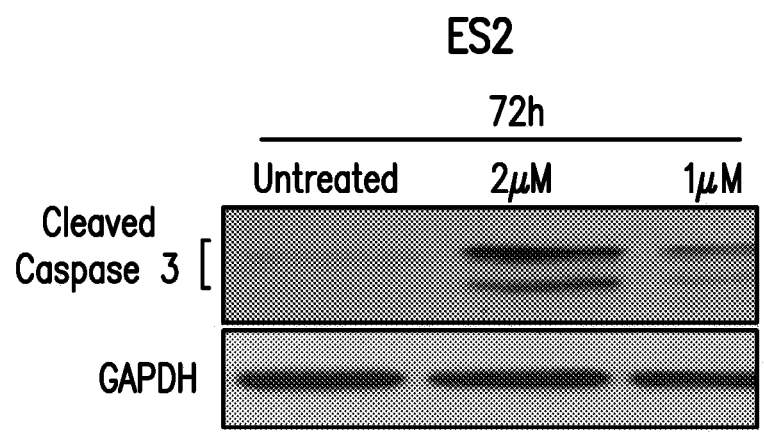
Figure 4E:
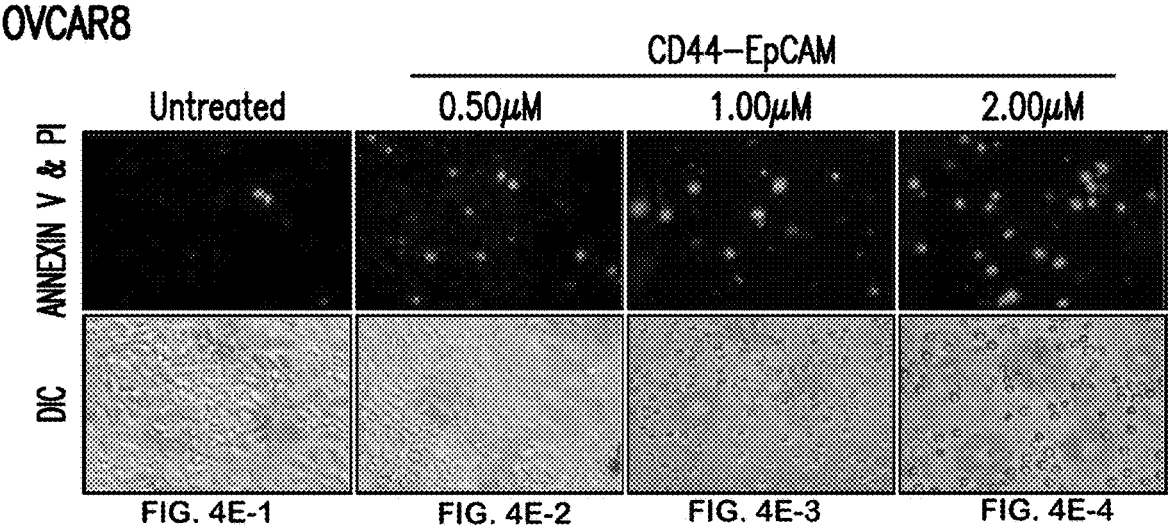
Figure 4F:
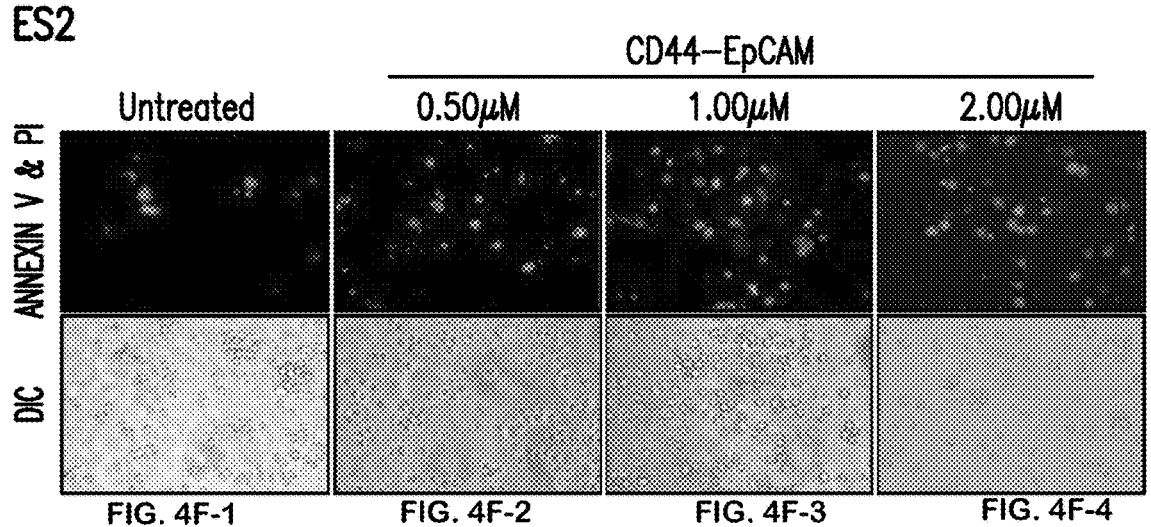

Example 5: Effect of Bispecific CD44-EpCAM Aptamer on Ovarian Cancer Cell Growth/Survival To explore if reduced cell viability by bispecific CD44-EpCAM aptamer was caused by apoptosis, the level of cleaved caspase-3, an indicator of apoptosis, was examined in cells treated with this aptamer for varying concentrations. Western blotting showed that treatment of bispecific CD44-EpCAM aptamer led to the appearance of cleaved caspase 3 (molecular weight 17 Kd and 19 Kd) in OVCAR8 and ES2 cells at 72 h (FIGS. 4A-4B). To further confirm the occurrence of apoptosis, OVCAR8 and ES2 cells treated with varying concentrations of bispecific CD44-EpCAM aptamer were subjected to Annexin V/Propidium Iodide (PI) staining-based flow cytometry. While the population of late stage apoptotic cell population (Annexin V+/PI+) was 1.56% in control OVCAR8 cells, this population was increased to 18.89% in cells treated with 2 µM bispecific CD44-EpCAM aptamer (FIGS. 4C-1-4C-4). Similarly, population of late apoptotic cells was increased from 2.54% in control to 19.58% in ES2 cells treated with bispecific CD44-EpCAM aptamer (FIGS. 4D-1-4D-4). The apoptotic pattern was also demonstrated from fluorescence microscope imaging (FIGS. 4E-1-4E-4 and 4F-1-4F-4). Compared with untreated controls, CD44-EpCAM treated OVCAR8 and ES2 cells have increased apoptosis signals of green (Annexin V) and red (PI) in a dose-dependent manner. These results suggest that bispecific CD44-EpCAM aptamer can effectively induce apoptosis in ovarian cancer cells.

Example 6: Biodistribution and Tumor Targeting Capability

Figure 5A:
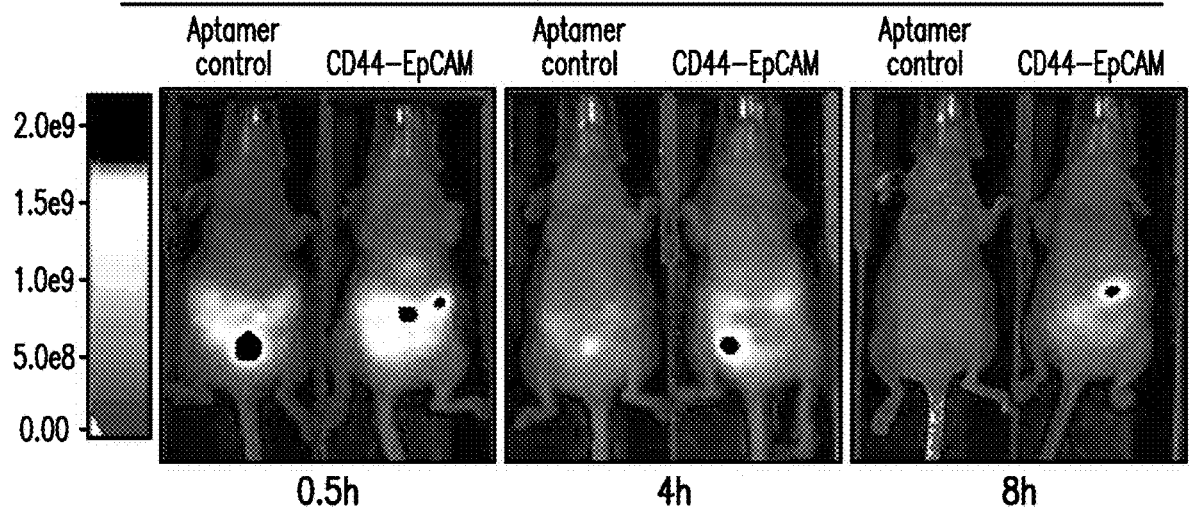
FIGS. 5A-5D show the biodistribution assay.
Figure 5B:
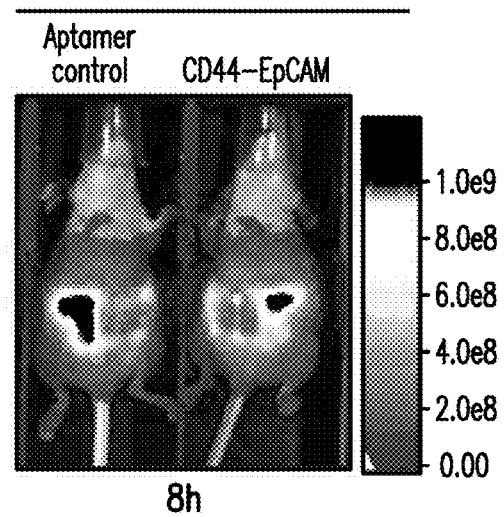
Figure 5C:
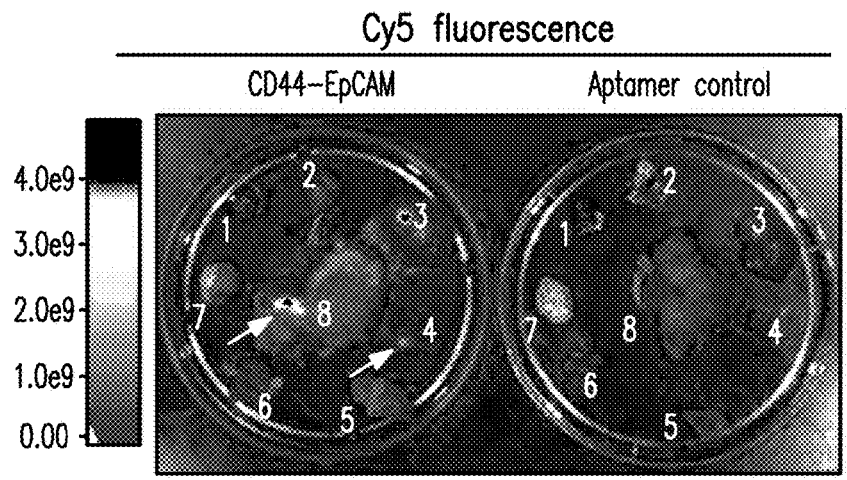
Figure 5D:
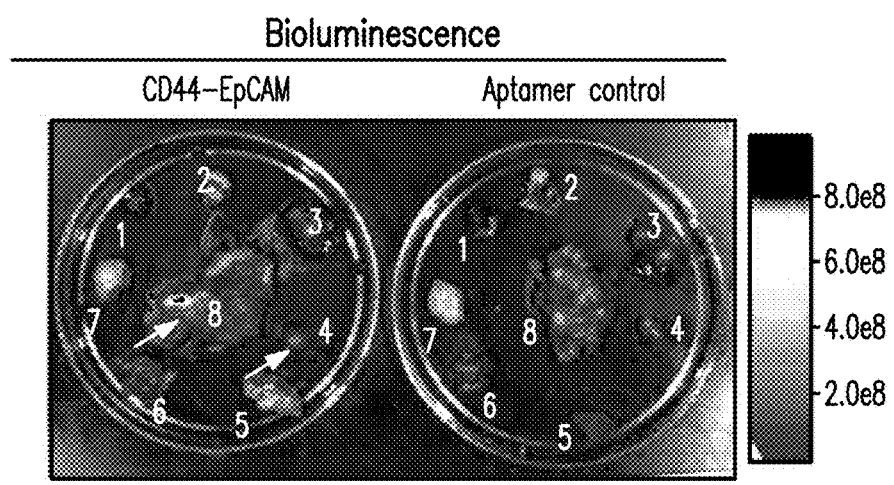

Female athymic nude mice were intraperitoneally injected with OVCAR8-Luc cells ($5\times10^6$/mouse). 8-days after injection of OVCAR8-Luc cells, Cy5-labeled CD44-EpCAM aptamer and Cy5-labeled non-targeting control MG aptamer were intraperitoneally injected to tumor bearing mice. At time points of 0.5 h, 4 h and 8 h, Cy5 fluorescence of mice were detected with Xenogen IVIS100 imaging system to monitor aptamer distribution in whole body. After 8-h injection of aptamers, mice were injected with luciferin for bioluminescence imaging. Bioluminescence images were captured following Cy5 fluorescence imaging with Xenogen IVIS 100. Bioluminescence shows the distribution profile of OVCAR8 tumor cells. As shown in FIGS. 5A-1-5A-3, after 4-h aptamer injection, non-targeting aptamer has shown the decreased Cy5 fluorescence compared with CD44-EpCAM, and was almost invisible post 8-h injection, while CD44-EpCAM still kept strong Cy5 fluorescence at 8 h. Bioluminescence imaging of whole body (FIG. 5B) demonstrated the distribution of tumor cells and confirmed that tumor cells spread in the entire peritoneum after 8-day implantation of OVCR8-luc tumor cells. Following whole body imaging, organs were removed and ex vivo images were captured. As shown in FIG. 5C, CD44-EpCAM aptamer (Cy5), but not non-targeting control aptamer, has greatly co-localized with spread tumors (bioluminescence). CD44-EpCAM aptamer was not observed in organs without tumors (brain, lung, heart). Notably, both CD44-EpCAM aptamer and control aptamer did not stagnate in kidney, that is different from nanoparticle-based materials (Liu et al., *Int J Nanomedicine,* 9:3509-3526 (2014); Huang et al., *Sci Rep,* 5:12458 (2015)).

The results indicate CD44-EpCAM aptamer does not bind to tumor-free organs and has strong tumor targeting capability.

Figure 6F:
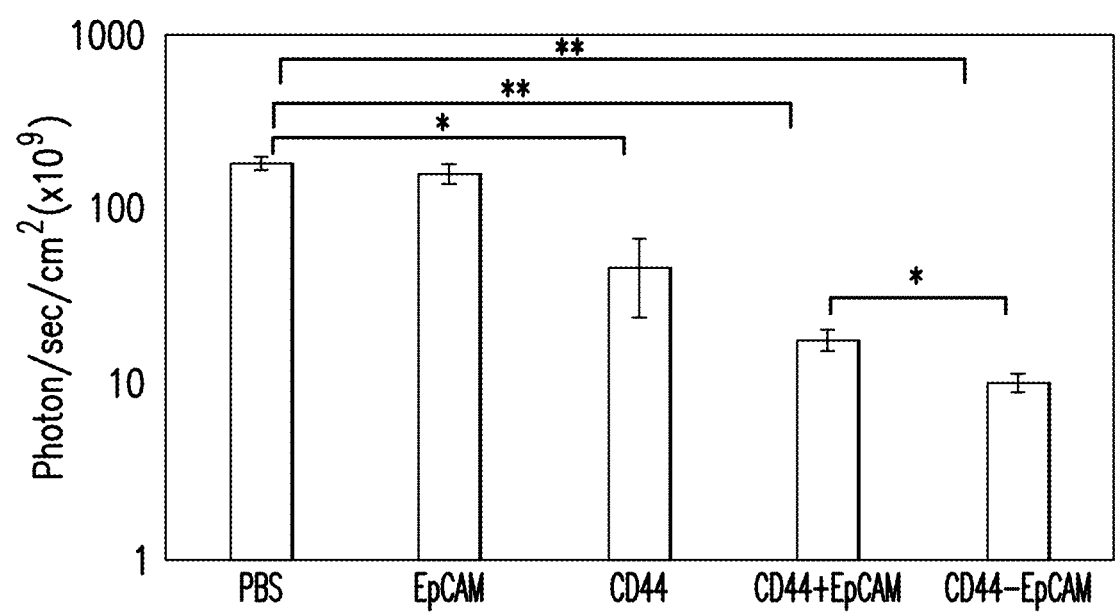

Example 7: Effect of Bispecific CD44-EpCAM Aptamer on Intraperitoneal Xenograft Development The ability of bispecific CD44-EpCAM aptamer to suppress ovary tumorigenesis was investigated. Female athymic nude mice were intraperitoneally injected with OVCAR8-Luc cells ($5\times10^6$/mouse). After 5 days, mice were intraperitoneally administered with PBS, single EpCAM aptamer, single CD44 aptamer, combination of single EpCAM and CD44 aptamer, and bispecific CD44-EpCAM aptamer at 2 nmoles per mouse every other day for first two weeks and every day for another two weeks. Bioluminescent imaging showed robust tumor growth in mice receiving PBS (FIGS. 6A and 6F). Single EpCAM aptamer treatment did not display treatment efficacy (FIGS. 6B and 6F). In contrast, single CD44 aptamer reduced tumor burden while the combined use of single CD44 and EpCAM aptamers retarded tumor growth even greater (FIGS. 6C, 6D, and 6F). Notably, bispecific CD44-EpCAM aptamer decreased tumor growth much more significantly than either single aptamer alone or together (FIGS. 6E and 6F). The increased efficacy is likely due to increased circulation life time of the larger molecular weight of the fused aptamer compared to lower molecular weight of single aptamers.

Figure 7A:
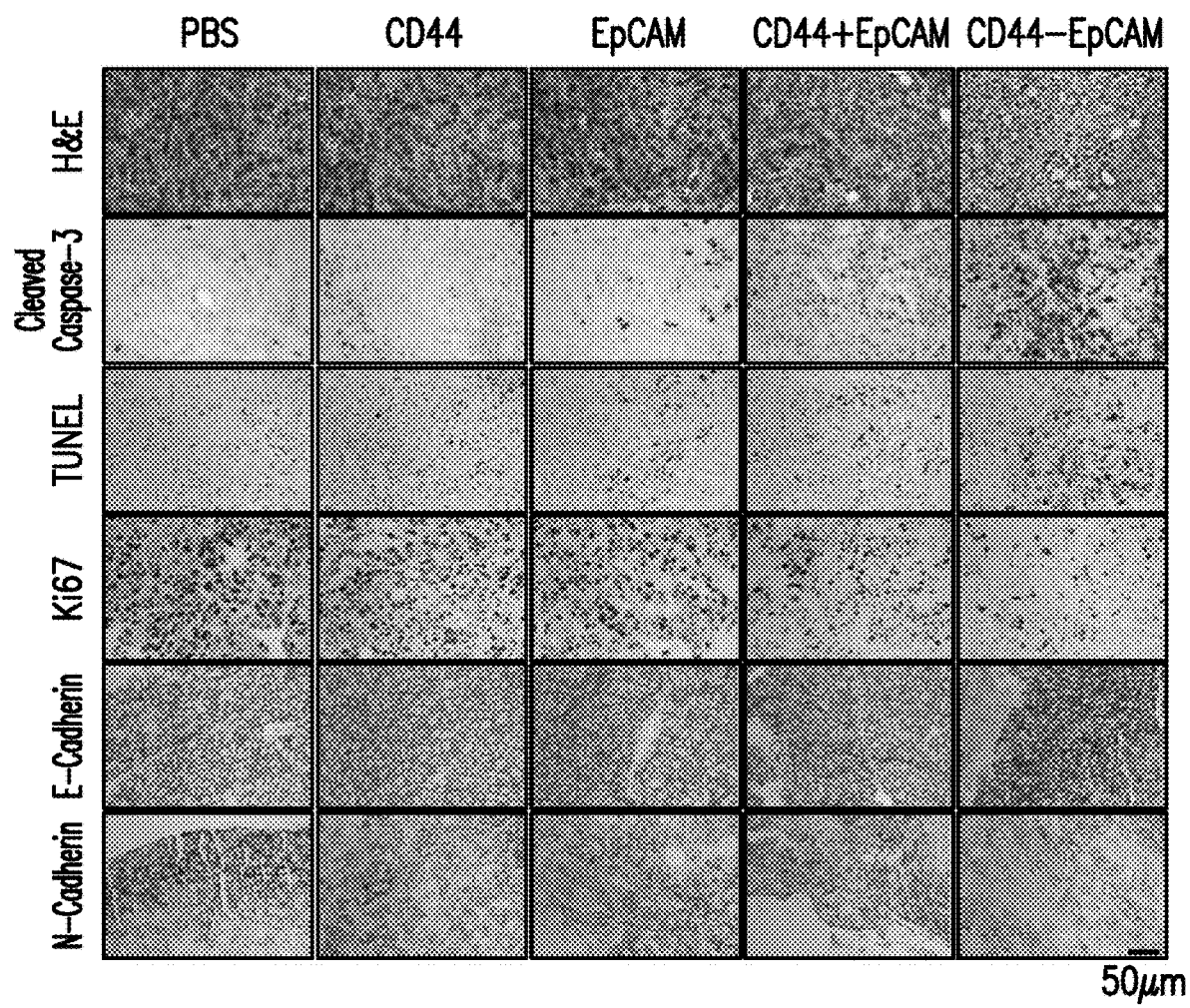
FIGS. 7A-7F show histology analysis of tumor and detection of biomarkers associated with apoptosis and metastasis by immunohistochemistry.
Figures 7B, 7C, 7D, 7E, 7F:
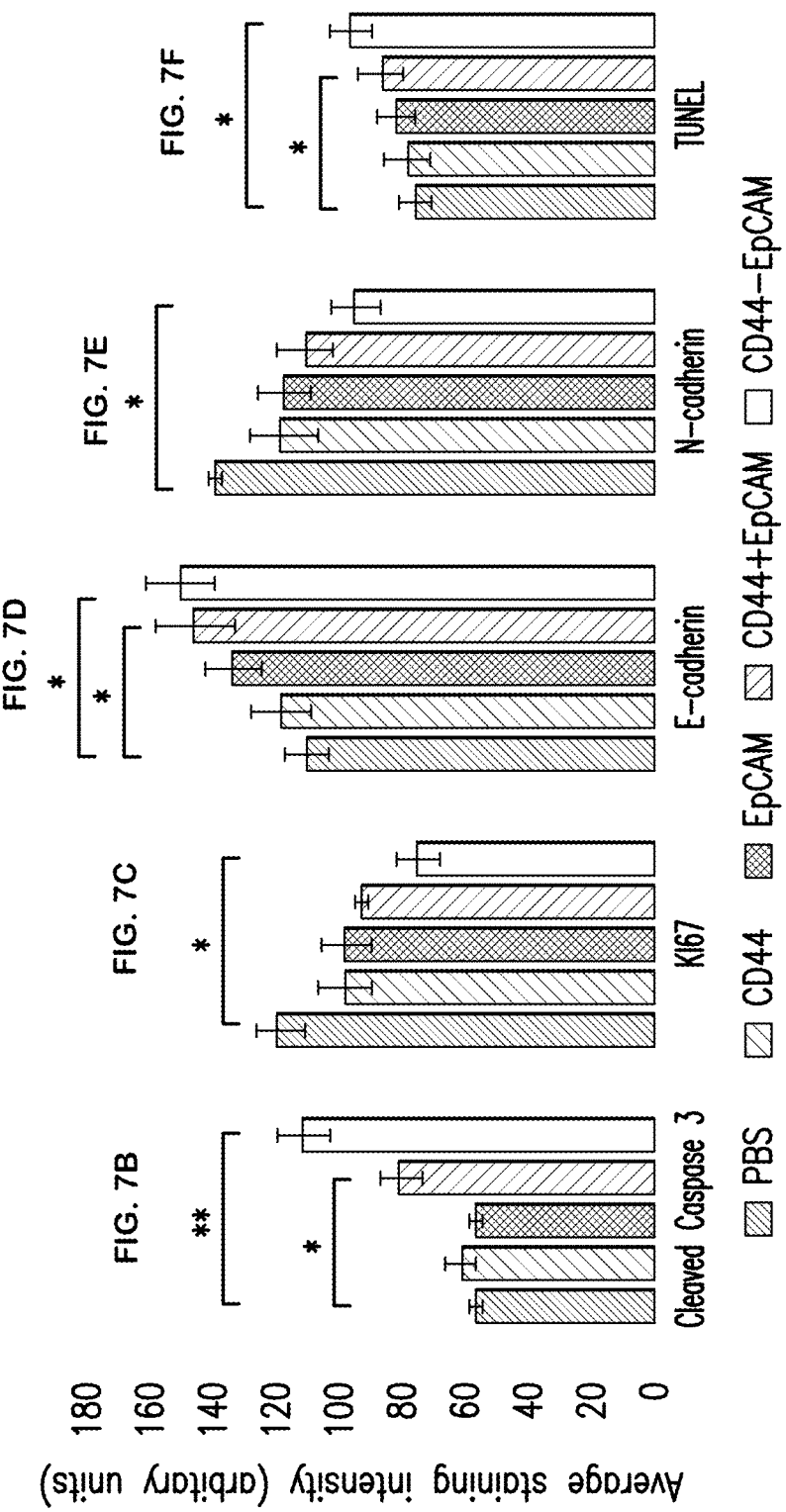

To elucidate the molecular mechanism underlying bispecific CD44-EpCAM aptamer-led inhibition in intraperitoneal tumor growth, H&E staining was performed on tumor implants collected from sacrificed mice. Compared with control, bispecific CD44-EpCAM aptamer-treated tumors were highly vacuolated and contained highly condensed nucleus and cytoplasm (FIG. 7A). Moreover, there were increased number of cells with body shrinkage and cells in specimens were loosely contacted with the neighboring cells in bispecific CD44-EpCAM aptamer-treated tumors. To link the observed histological alteration to the occurrence of apoptosis, immunohistochemistry staining of cleaved caspase 3 and TUNEL (Terminal deoxynucleotidyl transferase dUTP nick end labeling) was performed. The staining intensity of cleaved caspase-3 and TUNEL was much greater in bispecific CD44-EpCAM aptamer-treated tumors than all other treatment groups (FIGS. 7B-7F). This is consistent with the observation that bispecific CD44-EpCAM aptamer was able to induce apoptosis in ovarian cancer cells (FIGS. 4A-4F). Moreover, it was observed that the staining intensity of proliferation marker Ki67 was greatly decreased in bispecific CD44-EpCAM aptamer-treated tumors (FIG. 7B). These results suggest that bispecific CD44-EpCAM aptamer-led inhibition of intraperitoneal tumor progression results from triggering tumor cell apoptosis.

Whether CD44-EpCAM aptamer inhibition of ovarian cancer peritoneal metastasis is also through interfering epithelial-mesenchymal transition (EMT), which contributes to early-stage migration of cancer cells and is indispensable for invasion and metastasis of cancer cells was investigated. EMT is characterized by reduced E-cadherin and increased N-cadherin expression. Through IHC staining, it was found that upon treated with CD44-EpCAM aptamer, the expression of E-Cadherin increased (FIG. 7D) and expression of N-Cadherin decreased (FIG. 7E). That indicates that the inhibition of metastasis of CD44-EpCAM aptamer is also through reversal of EMT in addition to inducing apoptosis.

Example 8: Assessment of Bispecific CD44-EpCAM Aptamer Toxicity

Figure 8A:
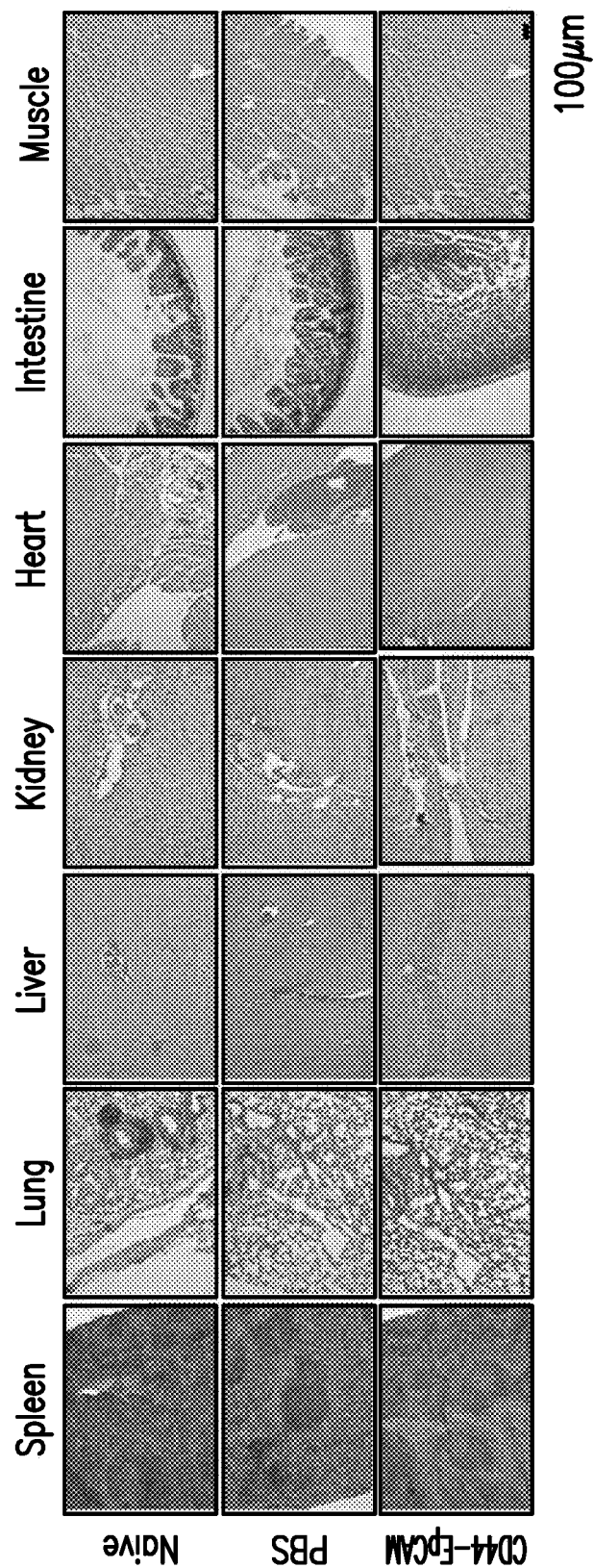
FIGS. 8A-8C show the assessment of bispecific CD44-EpCAM aptamer toxicity in major tissues.

The promise of using bispecific CD44-EpCAM aptamer to suppress ovarian tumor growth led us to further assess the potential toxicity of this aptamer to the host. All major organs including spleen, liver, kidney, heart, intestine and muscle were collected from sacrificed mice and carried out histology examinations on these organs. H&E staining showed that there was no obvious histological difference among untreated, PBS- and bispecific CD44-EpCAM aptamer-treated mice (FIG. 8A), suggesting that bispecific CD44-EpCAM aptamer is well tolerated by the host and can be safely used.

Figure 8B:
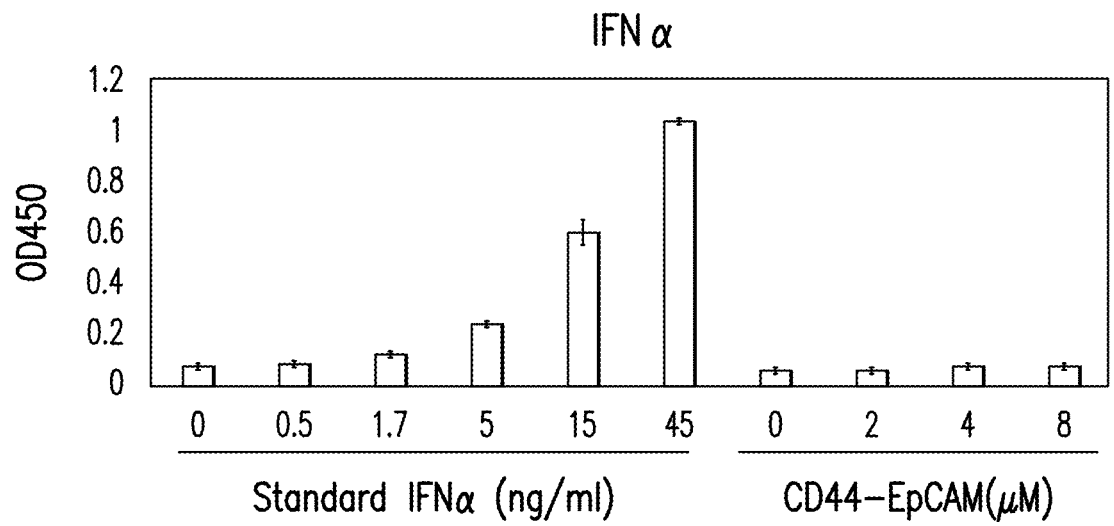
Figure 8C:
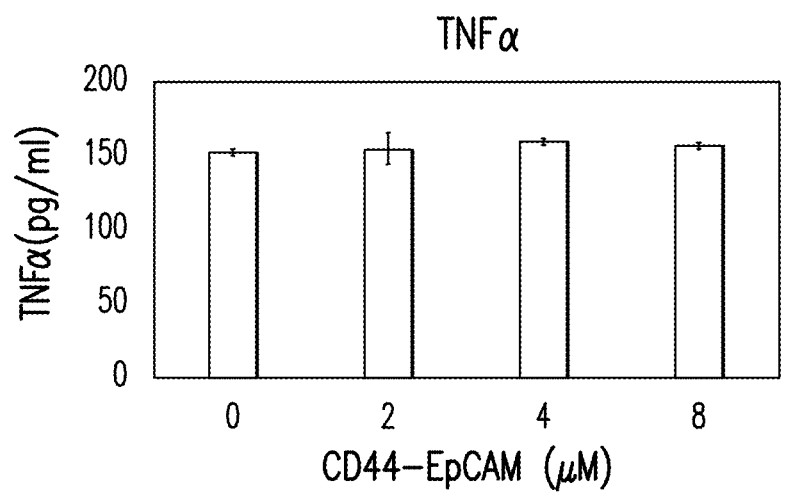

Exogenous RNA has been shown to induce innate immunogenicity-associated interferon upregulation (Kim et al., Nat Biotechnol, 22:321-325 (2004)). To determine the effect of bispecific CD44-EpCAM aptamer on innate immunogenicity, human peripheral mononuclear cells were treated with bispecific CD44-EpCAM aptamer for 24 h followed by evaluation of the amount of IFNα and TNFα released from these cells. ELISA showed that, at the concentration up to 8 μM, there was no detectable elevation in the level of IFNα or TNFα over the untreated control (FIGS. 8B and 8C). Taken together, these results suggest that nucleic acid-based bispecific CD44-EpCAM aptamer has no toxicity to the host and does not trigger innate immune response.

I claim:

1. A bispecific aptamer comprising a first end that specifically binds to a first tumor specific marker and a second end that specifically binds to a second tumor specific marker, wherein the first tumor specific marker is EpCAM and the second tumor specific marker is CD44, and further comprising one or more siRNA that downregulate an oncogene and wherein the oncogene is encoded by an oncogene selected from the group consisting of ABL1, ABL2, AKT1, AKT2, ATF1, BCL11A, BCL2, BCL3, BCL6, BCR, BRAF, CARD11, CBLB, CBLC, CCND1, CCND2, CCND3, CDX2, CTNNB1, DDB2, DDIT3, DDX6, DEK, ELK4, ERBB2, ETV4, ETV6, EVI1, EWSR1, FEV, FGFR1, FGFR1OP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCL1, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCL1A, TET2, TFG, MLL, TLX, TPR, and USP6.

2. The bispecific aptamer of claim 1, further comprising an unpaired linker.

3. The bispecific aptamer of claim 1, wherein the oncogene comprises AKT1.

4. The bispecific aptamer of claim 1, wherein the oncogene comprises BRAF.

5. The bispecific aptamer of claim 1, wherein the aptamer includes 2' fluoro-modified nucleotides.

6. A composition comprising a bispecific aptamer having a first end that specifically binds to tumor specific marker EpCAM and a second end that specifically binds to tumor specific marker CD44 and further comprising one or more siRNA that downregulate an AKT1 oncogene and wherein the composition further comprises a pharmaceutically acceptable excipient.

7. The composition of claim 6 wherein the bispecific aptamer is administered to a subject in need thereof in an amount effective to inhibit or reduce tumor growth.

8. The composition of claim 7 wherein the bispecific aptamer is administered in an amount effective to inhibit or reduce ovarian tumor growth.

* * * * *